(12) United States Patent
Ferguson et al.

(10) Patent No.: US 8,427,325 B2
(45) Date of Patent: *Apr. 23, 2013

(54) HUMAN MOVEMENT MEASUREMENT SYSTEM

(75) Inventors: Kevin Ferguson, Dublin, OH (US); Donald Gronachan, Holtsville, NY (US)

(73) Assignee: Motiva LLC, Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,126

(22) Filed: Mar. 23, 2012

(65) Prior Publication Data

US 2012/0178534 A1    Jul. 12, 2012

Related U.S. Application Data

(63) Continuation of application No. 13/096,587, filed on Apr. 28, 2011, now Pat. No. 8,159,354, which is a continuation of application No. 12/371,711, filed on Feb. 16, 2009, now Pat. No. 7,952,483, which is a continuation of application No. 11/935,578, filed on Nov. 6, 2007, now Pat. No. 7,492,268, which is a continuation of application No. 11/187,373, filed on Jul. 22, 2005, now Pat. No. 7,292, 151.

(60) Provisional application No. 60/592,092, filed on Jul. 29, 2004.

(51) Int. Cl.
*G08B 23/00* (2006.01)

(52) U.S. Cl.
USPC .............. 340/573.1; 340/5.61; 340/12.22; 345/161; 463/36; 434/114

(58) Field of Classification Search .............. 340/573.1, 340/5.61, 12.22, 691.2, 692; 345/156, 161; 463/36, 37; 434/114
See application file for complete search history.

(56) References Cited

U.S. PATENT DOCUMENTS

| 4,337,049 A | 6/1982 | Connelly |
| 4,375,674 A | 3/1983 | Thornton |
| 4,627,620 A | 12/1986 | Yang |
| 4,631,676 A | 12/1986 | Pugh |
| 4,645,458 A | 2/1987 | Williams |
| 4,695,953 A | 9/1987 | Blair et al. |
| 4,702,475 A | 10/1987 | Elstein et al. |

(Continued)

FOREIGN PATENT DOCUMENTS

| EP | 0993845 | 12/2005 |
| JP | 2000308756 | 11/2000 |

(Continued)

OTHER PUBLICATIONS

Allard, P., et al, Three-Dimensional Analysis of Human Movement, Human Kinetics (1995) 3, 8-14.

(Continued)

*Primary Examiner* — Toan N Pham
(74) *Attorney, Agent, or Firm* — Standley Law Group LLP

(57) ABSTRACT

A system for use in playing a video game, the system acting to measure the movement, motion, acceleration, orientation, and/or position of transponders while being guided by interactive and sensory feedback. A bidirectional communication link to a processing system supporting the video game provides functional movement assessment.

107 Claims, 10 Drawing Sheets

U.S. PATENT DOCUMENTS

| | | |
|---|---|---|
| 4,751,642 A | 6/1988 | Silva et al. |
| 4,787,051 A | 11/1988 | Olson |
| 4,817,950 A | 4/1989 | Goo |
| 4,912,638 A | 3/1990 | Pratt |
| 4,925,189 A | 5/1990 | Braeunig |
| 4,988,981 A | 1/1991 | Zimmerman |
| 5,148,154 A | 9/1992 | MacKay et al. |
| 5,184,295 A | 2/1993 | Mann |
| 5,214,615 A | 5/1993 | Baur |
| 5,227,985 A | 7/1993 | DeMenthon |
| 5,229,756 A | 7/1993 | Kosugi et al. |
| 5,239,463 A | 8/1993 | Blair |
| 5,255,211 A | 10/1993 | Redmond |
| 5,288,078 A | 2/1994 | Capper et al. |
| 5,296,871 A | 3/1994 | Paley |
| 5,320,538 A | 6/1994 | Baum |
| 5,347,306 A | 9/1994 | Nitta |
| 5,372,365 A | 12/1994 | McTeigue et al. |
| 5,375,610 A | 12/1994 | LaCourse et al. |
| 5,385,519 A | 1/1995 | Hsu et al. |
| 5,405,152 A | 4/1995 | Katanics et al. |
| 5,421,590 A | 6/1995 | Robbins |
| 5,423,554 A | 6/1995 | Davis |
| 5,429,140 A | 7/1995 | Burdea |
| 5,466,200 A | 11/1995 | Uerich |
| 5,469,740 A | 11/1995 | French et al. |
| 5,474,083 A | 12/1995 | Church et al. |
| 5,485,402 A | 1/1996 | Smith et al. |
| 5,495,576 A | 2/1996 | Ritchey |
| 5,506,605 A | 4/1996 | Paley |
| 5,516,105 A | 5/1996 | Eisenbrey et al. |
| 5,524,637 A | 6/1996 | Erickson |
| 5,554,033 A | 9/1996 | Bizzi et al. |
| 5,574,479 A | 11/1996 | Odell |
| 5,577,981 A | 11/1996 | Jarvik |
| 5,580,249 A | 12/1996 | Jacobsen et al. |
| 5,584,700 A | 12/1996 | Feldnian |
| 5,587,937 A | 12/1996 | Massie |
| 5,591,104 A | 1/1997 | Andrus et al. |
| 5,597,309 A | 1/1997 | Riess |
| 5,602,569 A | 2/1997 | Kato |
| 5,605,505 A | 2/1997 | Han |
| 5,616,078 A | 4/1997 | Oh |
| 5,638,300 A | 6/1997 | Johnson |
| 5,641,288 A | 6/1997 | Zaenglein, Jr. |
| 5,645,077 A | 7/1997 | Foxlin |
| 5,656,904 A | 8/1997 | Lander |
| 5,659,691 A | 8/1997 | Durward et al. |
| 5,679,004 A | 10/1997 | McGowan et al. |
| 5,702,323 A | 12/1997 | Poulton |
| 5,703,623 A | 12/1997 | Hall |
| 5,704,837 A | 1/1998 | Iwasaki et al. |
| 5,711,304 A | 1/1998 | Dower |
| 5,715,834 A | 2/1998 | Bergamasco et al. |
| 5,720,619 A | 2/1998 | Fisslinger |
| 5,759,044 A | 6/1998 | Redmond |
| 5,785,630 A | 7/1998 | Bobick |
| 5,785,631 A | 7/1998 | Heidecke |
| 5,790,076 A | 8/1998 | Sypniewski |
| 5,790,124 A | 8/1998 | Fischer et al. |
| 5,792,031 A | 8/1998 | Alton |
| 5,796,354 A | 8/1998 | Cartabiano et al. |
| 5,812,257 A | 9/1998 | Teitel et al. |
| 5,835,077 A | 11/1998 | Dao et al. |
| 5,838,816 A | 11/1998 | Holmberg |
| 5,846,086 A | 12/1998 | Bizzi et al. |
| 5,850,201 A | 12/1998 | Lasko-Harvil |
| 5,872,438 A | 2/1999 | Roston |
| 5,875,257 A | 2/1999 | Marrin et al. |
| 5,888,172 A | 3/1999 | Andras et al. |
| 5,890,995 A | 4/1999 | Bobick |
| 5,897,437 A | 4/1999 | Nishiumi et al. |
| 5,913,727 A | 6/1999 | Andoot |
| 5,919,149 A | 7/1999 | Allum |
| 5,929,782 A | 7/1999 | Stark et al. |
| 5,963,891 A | 10/1999 | Walker et al. |
| 5,986,644 A | 11/1999 | Herder |
| 5,989,157 A | 11/1999 | Walton |
| 5,991,693 A | 11/1999 | Zalewski |
| 6,004,243 A | 12/1999 | Ewart |
| 6,013,007 A | 1/2000 | Root et al. |
| 6,028,593 A | 2/2000 | Rosenberg et al. |
| 6,043,873 A | 3/2000 | Ramer et al. |
| 6,050,822 A | 4/2000 | Faughnn |
| 6,050,963 A | 4/2000 | Johnson et al. |
| 6,054,951 A | 4/2000 | Sypniewski |
| 6,059,576 A | 5/2000 | Brann |
| 6,066,075 A | 5/2000 | Poulton |
| 6,073,489 A | 6/2000 | French et al. |
| 6,077,201 A | 6/2000 | Cheng |
| 6,088,091 A | 7/2000 | Ramer |
| 6,098,458 A | 8/2000 | French et al. |
| 6,100,896 A | 8/2000 | Strohecker et al. |
| 6,119,516 A | 9/2000 | Hock |
| 6,132,337 A | 10/2000 | Krupka et al. |
| 6,152,856 A | 11/2000 | Studor |
| 6,160,540 A | 12/2000 | Fishkin |
| 6,162,191 A | 12/2000 | Foxlin |
| 6,164,973 A | 12/2000 | Macri |
| 6,181,343 B1 | 1/2001 | Lyons |
| 6,182,169 B1 | 1/2001 | Force |
| 6,183,259 B1 | 2/2001 | Macri |
| 6,198,528 B1 | 3/2001 | Maynard |
| 6,200,253 B1 | 3/2001 | Nishiumi et al. |
| 6,211,861 B1 | 4/2001 | Rosenberg et al. |
| 6,241,612 B1 | 6/2001 | Heredia |
| 6,244,987 B1 | 6/2001 | Ohsuga |
| 6,304,250 B1 | 10/2001 | Yang et al. |
| 6,308,565 B1 | 10/2001 | French et al. |
| 6,315,673 B1 | 11/2001 | Kopera et al. |
| 6,346,045 B2 | 2/2002 | Rider |
| 6,361,507 B1 | 3/2002 | Foxlin |
| 6,366,272 B1 | 4/2002 | Rosenberg et al. |
| 6,377,793 B1 | 4/2002 | Jenkins |
| 6,400,452 B1 | 6/2002 | Maynard |
| 6,415,223 B1 | 7/2002 | Lin et al. |
| 6,424,333 B1 | 7/2002 | Tremblay et al. |
| 6,430,997 B1 | 8/2002 | French et al. |
| 6,487,906 B1 | 12/2002 | Hock |
| 6,515,593 B1 | 2/2003 | Stark et al. |
| 6,545,661 B1 | 4/2003 | Goschy et al. |
| 6,554,781 B1 | 4/2003 | Carter et al. |
| 6,582,380 B2 | 6/2003 | Kazlausky et al. |
| 6,590,536 B1 | 7/2003 | Walton |
| 6,592,461 B1 | 7/2003 | Raviv |
| 6,605,038 B1 | 8/2003 | Teller et al. |
| 6,616,607 B2 | 9/2003 | Hashimoto et al. |
| 6,676,520 B2 | 1/2004 | Nishiumi et al. |
| 6,682,351 B1 | 1/2004 | Abraham-Fuchs |
| 6,712,692 B2 | 3/2004 | Basson et al. |
| 6,717,573 B1 | 4/2004 | Shahonian et al. |
| 6,720,876 B1 | 4/2004 | Burgess |
| 6,749,432 B2 | 6/2004 | French et al. |
| 6,757,068 B2 | 6/2004 | Foxlin |
| 6,765,726 B2 | 7/2004 | French et al. |
| 6,774,885 B1 | 8/2004 | Even-Zohar |
| 6,811,491 B1 | 11/2004 | Levenberg |
| 6,834,436 B2 | 12/2004 | Townsend et al. |
| 6,850,844 B1 | 2/2005 | Walters et al. |
| 6,872,139 B2 | 3/2005 | Sato et al. |
| 6,876,496 B2 | 4/2005 | French et al. |
| 6,881,147 B2 | 4/2005 | Naghi |
| 6,990,639 B2 | 1/2006 | Wilson |
| 7,000,469 B2 | 2/2006 | Foxlin et al. |
| 7,127,370 B2 | 10/2006 | Kelly et al. |
| 7,158,118 B2 | 1/2007 | Liberty |
| 7,182,691 B1 | 2/2007 | Schena |
| 7,183,480 B2 | 2/2007 | Nishitani et al. |
| 7,220,220 B2 | 5/2007 | Stubbs et al. |
| 7,236,156 B2 | 6/2007 | Liberty et al. |
| 7,239,301 B2 | 7/2007 | Liberty et al. |
| 7,261,690 B2 | 8/2007 | Teller et al. |
| 7,262,760 B2 | 8/2007 | Liberty |
| 7,292,151 B2 | 11/2007 | Ferguson |
| 7,301,648 B2 | 11/2007 | Foxlin |
| 7,335,134 B1 | 2/2008 | LaVelle |
| 7,359,121 B2 | 4/2008 | French et al. |

| | | |
|---|---|---|
| 7,414,611 B2 | 8/2008 | Liberty |
| 7,492,268 B2 | 2/2009 | Ferguson |
| 7,952,483 B2* | 5/2011 | Ferguson et al. .......... 340/573.1 |
| 8,159,354 B2* | 4/2012 | Ferguson et al. .......... 340/573.1 |
| 2001/0015123 A1 | 8/2001 | Nishitani et al. |
| 2002/0024675 A1 | 2/2002 | Foxlin |
| 2002/0126026 A1 | 9/2002 | Lee |
| 2002/0183961 A1 | 12/2002 | French et al. |
| 2004/0034289 A1 | 2/2004 | Teller et al. |
| 2004/0070564 A1 | 4/2004 | Dawson et al. |
| 2004/0140954 A1 | 7/2004 | Faeth |
| 2005/0020369 A1 | 1/2005 | Davis et al. |
| 2005/0032582 A1 | 2/2005 | Mahajan |
| 2005/0054457 A1 | 3/2005 | Eyestone |
| 2006/0028446 A1 | 2/2006 | Liberty et al. |
| 2006/0122474 A1 | 6/2006 | Teller et al. |
| 2007/0173705 A1 | 7/2007 | Teller et al. |

FOREIGN PATENT DOCUMENTS

| | | |
|---|---|---|
| JP | 2002-82751 | 3/2002 |
| JP | 2003053038 | 2/2003 |
| JP | 2003325974 | 11/2003 |
| WO | WO9712337 | 4/1997 |
| WO | PCT/US9617580 | 5/1997 |
| WO | 0035345 | 6/2000 |
| WO | WO0047108 | 8/2000 |
| WO | WO0187426 | 11/2001 |
| WO | 03015005 | 2/2003 |
| WO | 2004039055 | 5/2004 |

OTHER PUBLICATIONS

Brownstein, B., et al, Functional Movement in Orthopedic and Sports Physical Therapy, Churchill Livingstone (1997), 15.
Brugger, W., et al, Computer-aided tracking of body motions using a c.c.d.-image sensor, Med. Biol. Eng. & Comput, (Mar. 1978), 207-210.
Codella, C., et al, Interactive Simulation in a Multi-Person Virtual World ACM (May 3-7, 1992), 329-334.
DeLoura, M., et al, Game Programming Gems, Charles River Media, (2000) 200-204.
Greenleaf, W.J., DataGlove, DataSuit, and virtual reality Advanced technology for people with disabilities, Proceedings of the Seventh Annual Conference 'Technology and Persons with Disabilities,' (Mar. 1992) 211-214.
Kasvand, T., et al, Computers and the Kinesiology of Gait, Comput. Biol. Med. Pergamon Press (1976) vol. 6 111-120.
Kenmochi, A., et al, A network virtual reality skiing system-system overview and skiing movement estimation, Symbiosis of Human and Artifact, (Jul. 1995) 423-428.
Kraus, A., Matrices for Engineers, Hemisphere Publishing Corp. (1987) 118-120, 124-126.
Lengyel, E., Mathematics for 3D Game Programming & Computer Graphics, Charles River Media (2004) 76-78, 467-468.
Medved, V., Towards a virtual reality-assisted movement diagnostics—an outline, Robotica (Jan.-Feb. 1994) vol. 12, 55-57.
Mulder, A., Human movement tracking technology, School of Kinesiology, Simon Fraser University (Jul. 1994) 1-14.
Ruby, D., Biomechanics—how computers extend athletic performance to the body's far limits, Popular Science (Jan. 1982) 58-60.
Sandweiss, J., et al, Biofeedback and Sports Science, Plenum Press New York (1985) 1-201.
Scarborough, E.L., Enhancement of Audio Localization Cue Synthesis by Adding Environmental and Visual Cues, Air Force Inst. of Tech., Wright-Patterson AFB, OH. School of Engineering (Dec. 1992) 1-4.
Smith, J., et al, Virtual Batting Cage and Human Model, Virtual Human http://www.cs.berkeley.edu/rcdavis/classes/cs294/, (Jun. 17, 2004)1-5.
Zetu, D., et al, Extended range tracking for remote virtual reality-aided facility management, Department of Mechanical Engineering The University of Illinois at Chicago, http://alpha.me.uic.edu/dan/NsfPaper/nsf2.html, (Apr. 19, 2004)1-9.
Codamotion: The science of real-time motion capture and analysis, webpages from http://www.charndyn.com/index.html, (Apr. 17, 2004) 1.
Irex, Virtual Reality Technologies, webpages from http://www.irexonline.com/how_it_works.htm, (Apr. 19, 2004) 1-2.
Polhemus, Patriot: The Fast and Affordable Digital Tracker, www.polhemus.com, (Feb. 2004) 1-2.
Polhemus, Liberty: The Forerunner in Electromagnetic Tracking Technology, www.polhemus.com, (May 2003) 1-2.
Success Story Profile: Innovative Sports Training, Motion Monitor, (2002) 1-2.
Reality built for two: a virtual reality tool, Symposium on Interactive 3D Graphics, ACM Press webpages from http://portal.acm.org/citation.cfm?id=91385.91409&dl+ACM&type=series&i (Jun. 10, 2004) 1-4.
Europe is Bursting with Virtual Reality Ideas, But Developers are Critically Strapped for Cash, webpages from https://www/lexis.com/research/retrieve?_m=66d17057c1b77f197aledb9f5fadb87d&_browseType=Text, (Jan. 1993) 1-2.
Wilson et al, "Gesture Recognition Using the XWand," Assistive Intelligent Environments Group, Robotics Institute, Carnegie Mellon University, Report CMU-RI-TR-04-57 (Apr. 2004).
Wilson et al, "XWand: UI for Intelligent Spaces," Microsoft Research, inProceedings of the SIGCHI Conference on Human Factors in Computing Systems (Ft. Lauderdale, Florida, USA, Apr. 5-10, 2003; CHI '03, ACM, New York, NY, at 545-52 (2003).
Hinckley Synchronous Gestures Device, Oct. 12-15, 2003, Microsoft Research, USA.
SmartSwing, SmartSwing Inc.,Apr. 2004, Austin, Texas.
Mulder, Axel, "Human movement tracking technology," Hand Centered Studies of Human Movement Project, Technical Report 94-1, Simon Fraser University (Jul. 1994), 16 pages.
Furniss, Maureen, "Motion Capture," MoCap MIT (Dec. 1999) 12 pages.
Nintendo N64 Rumble Pack, Nintendo, Jul. 1997, Wikipedia Article, 12 pages, http://en.wikipedia.org/wiki/Rumble_Pak.
Nintendo GameCube System, Nintendo, Nov. 18, 2001, Wikipedia Article, http://en.wikipedia.org/wiki/Nintendo_GameCube.
Nintendo GameCube Standard Controller, Nintendo, Nov. 18, 2001, Wikipedia Article, http://en.wikipedia.org/wiki/Nintendo_GameCube_Controller.
Bachman, E.R., Duman, I., Usta, U.Y., McGhee, R.B., Yun, X.P., Zyda, M.J.,"Orientation Tracking for Humans and Robots Using Inertial Sensors," 1999 IEEE International Symposium on Computational Intelligence in Robotics and Automation (CIRA99) at 187-94 (1999).
Nintendo "Kirby Tilt 'n' Tumble" video game, Nintendo, Apr. 11, 2001, Wikipedia Article, http:en.wikipedia.org/wiki/Kirby_Tilt_%27%_Tumble.
Benbsat, Ari Y., Paradiso, Joseph A., "An Inertial Measurement Framework for Gesture Recognition and Applications," Gesture and Sign Language in Human-Computer Interaction, vol. 2298/2002 at 77-90 (Springer-Verlag Berlin Heibelberg 2002); International Gesture Workshop, GW 2001, London, UK, 2001 Proceedings, LNAI 2298, at 9-20, I. Wachsmuth and T. Sowa (eds.).
Analog Devices Data Sheet, "MicroConverter®, Multichannel 12-Bit ADC with Embedded Flash MCU, ADuC812" (2003) (http://www.analog.com/static/imported-files/data_sheets/ADUC812.pdf) 60 pages.
MacLean, Karen, "Designing with Haptic Feedback", Proceedings of IEEE Robotics and Automation (ICRA '2000), at 783-88 (Apr. 22-28, 2000).
Wormell, D. and Foxlin, E., "Advancements in 3D Interactive Devices for Virtual Environments," EGVE, Proceedings of the Workshop on Virtual Environments 2003, vol. 39 at 47-56 (ACM) (2003) (The Eurographics Association).
Ballagas, Rafael; Ringel, Meredith; Stone Maureen; and Borchers, Jan, "iStuff: A Physical User Interface Toolkit for Ubiquitous Computer Environments," Proceedings of the SIGCHI Conference on Human Factors in Computing Systems, vol. 5, No. 1, at 537-44 (ACM) (Apr. 5-10, 2003) (Gilbert Cockton, Panu Korhonen, eds.).
Pelican Accessories G3 Wireless Controller, Pelican Accessories, Sep. 20, 2002.
Nintendo Wavebird Controller, Nintendo, Jun. 2002 Wikipedia Article, http://en.wikipedia.org/wiki/WaveBird.

Nintendo Game Boy, Nintendo,Jul. 31, 1989, Wikipedia Article, http://en.wikipedia.org/wiki/Game_Boy.

Nintendo Game Boy Advance, Nintendo, Sep. 26, 2003, Wikipedia Article http://en.wikipedia.org/wiki/Game_Boy_Advance.

Nintendo Game Boy Advance Wireless Adapter, Nintendo World Report, Sep. 25, 2003, 2 pages.

Nintendo Game Boy Color Nintendo, Nov. 18, 1998, Wikipedia Article http://en.wikipedia.org/wiki/Game_Boy_Color.

Nintendo Game Boy Color Game Catridge with Built-In Rumble, Nintendo, Jun. 28, 1999, Wikipedia Article, 2pages http://en.wikipedia.org/wiki/Rumble_Pak.

Verplaetse, C., "Inertial Proprioceptive Devices: Self-Motion-Sensing Toys and Tools," IBM Systems Journal, vol. 35 Nos. 3 & 4, at 639-50 (IBM Corp.) (1996).

Yang, Ungyeon and Kim, Gerard Jounghyun, "Implementation and Evaluation of 'Just Follow Me': An Ilmmersive, VR-Based, Motion-Training System," Presence: Teleoperators and Virtual Environments vol. 11 No. 3, at 304-23 (MIT Press) (Jun. 2002).

Hinckley, Ken et al, "Sensing Techniques for Mobile Interaction," Proceedings of the 13th Annual ACM Symposium on User Interface Software and Technology (San Diego, Cal.), ACM UIST 2000 & Technology, CHI Letters 2 (2), at 91-100 (2000).

Paradiso, Joseph A., "The Brain Opera Technology: New Instruments and Gestural Sensors for Musical Interaction and Performance" (Nov. 1998) ("Brain Opera Article").

CyberGlove product, Immersion Corporation, 1990, http://www.cyberglovesystem.com.

Kunz, Andreas and Burri, Adrian "Design and Construction of a New Haptic Interface," ASME 2000 Design Engineering Technical Conferences and Computers and Information in Engineering Conference, Baltimore, Maryland, Sep. 10-13, 2000; Proceedings of DETC '00.

Merians, Alma S. et al "Virtual Reality—Augmented Rehabilitation for Patients Following Stroke," Physical Therapy, vol. 82, No. 9 (Sep. 2002).

Logitech WingMan Cordless Rumblepad, Logitech, Press release Sep. 2, 2001, 2 pages.

InterSense, "Technical Overview IS-900 Motion Tracking System" www.isense.com, Apr. 2004.

Marrin, Teresa and Paradiso, Joseph, "The Digital Baton: a Versatile Performance Instrument" (1997).

Marrin, Teresa, "Toward an Understanding of Musical Gesture: Mapping Expressive Intention with the Digital Baton" (1996).

Hinckley, Ken, "Haptic Issues for Virtual Manipulation—A Dissertation Presented to the Faculty of the School of Engineering and Applied Science at the University of Virginia" (Dec. 1996).

Marti, Gaetan et al, "Biopsy navigator: a smart haptic interface for interventional radiological gestures," Swiss Federal Institute of Technology (EPFL), CARS 2003 (Computer Assisted Radiology and Surgery), Proceedings of the 17th Int'l Congress & Exhibition, International Congress Series, vol. 1256 at 788-93 (Jun. 2003).

Williams II, Robert L. et al, "The Virtual Haptic Back Project," Presented at the IMAGE 2003 Conference, Scottsdale, Arizona, Jul. 14-18, 2003.

PowerGlove product Program Guide, Mattel, 1989.

IS-900 product, InterSense, Inc. 1999.

Regan, Mary Beth, "Smart Golf Clubs", baltimoresun.com, Jun. 17, 2005.

FrontSide Field Test, "Smart Bomber Get This", Golf Magazine, Jun. 2005.

Achenbach, James, "Golf's New Measuring Stick", Golfweek, Jun. 11, 2005, www.golfweek.com.

Eyestone, Dick, "SmartSwing Company: Letter from the CEO", 3 pages, 2004, retrieved May 19, 2009, http://web.archive.org/web/20040810101314/www.smartsinggolf.com.

Training Aid, SmartSwing, PGA Magazine, p. 46, Apr. 2005, www.pgamagazine.com.

"MEMS enable smart golf clubs", Small Times, Jan. 6, 2005, 2 pages.

Swisher, Kara, "How Science Can Improve Your Golf Game", The Wall Street Journal, Apr. 18, 2005.

Smartswing, "Register to be Notified When SmartSwing Products are Available for Purchase", 3 pages, May 2004, retrieved May 19, 2009, http://web.archive.org/web/20040426182437/www.smartswinggolf.com/ . . . .

Smartswing, "SmartSwing: Intelligent Golf Clubs that Build a Better Swing", 2 pages, 2004, retrieved May 19, 2009, http://web.archive.org/web/20040728221951/http://www.smartswinggolf . . . .

Smartswing, The SmartSwing Learning System: How it works, 3 pages, 2004, retrieved May 19, 2009, http://web.archive.org/web/20040403213108/http://www.smartswinggolf.com/t . . . .

Smartswing, The SmartSwing Learning System Overview, 3 pages, 2004, retrieved May 19, 2009, http://web.archive.org/web/20040810142134/http://www.smartswinggolf.com/t . . . .

Smartswing, The SmartSwing Product, 3 pages, 2004, retrieved May 19, 2009, http://web.archive.org/web/200400403204628/http://www.smartswinggolf.com/t . . . .

Smartswing, The SmartSwing Product: Technical Information, 1 page, 2004, retrieved May 19, 2009, http://web.archive.org/web/200400403205906/http://www.smartswinggolf.com/ . . . .

Buchanan, Levi, "Happy Birthday, Rumble Pak", IGN.com, Apr. 3, 2008, 2 pages.

Fielder, Lauren, "E3 2001: Nintendo unleashes GameCube software, a new Miyamoto game, and more", GameSpot, May 16, 2001, 2 pages, http://www.gamespot.com/downloads/2761390.

Nintendo"Kirby Tilt 'n' Tumble" video game Instruction booklet, Nintendo, Apr. 11, 2001, 18 pages.

Nintendo Wavebird Controller, Operation of the WaveBird Controller Nintendo, Jun. 2002, 2 pages.

Wiley, M., "Nintendo Wavebird Review" US, Jun. 11, 2002, 21 pages.

Nintendo Game Boy, Consumer Information and Precautions Booklet, Nintendo,Jul. 31, 1989.

Logitech 3D Mouse & Head Tracker Technical Manual, Logitech Inc., Fremont CA, 1992, 88 pages.

Sulic, Ivan, Logitech Wingman Cordless Rumblepad Review, IGN Entertainment Games, Jan. 14, 2002, 3 pages.

Immersion CyberGlove product, Immersion Corporation, 1990, http://www.cyberglovesystem.com.

InterSense, "IS-900 Precision Motion Trackers" www.isense.com May 16, 2003.

InterSense, "InterSense Motion Trackers" www.isense.com Mar. 12, 1998.

InterSense, "InterSense Inc.—The New Standard in Motion Tracking" www.isense.com Mar. 27, 2004.

InterSense, "InterSense Inc.—The New Standard in Motion Tracking" www.isense.com Dec. 18, 2003.

InterSense, "IS-900 Precision Motion Trackers" www.isense.com Sep. 10, 2002.

Williams II, Robert L. et al, "Implementation and Evaluation of a Haptic Playback System," vol. 3, No. 3, Haptics-e, 2004, http://www.haptics-e.org.

PowerGlove product, Mattel, 1989 Wikipedia Article.

PowerGlove and Nintendo product photo, Mattel, 1989.

PowerGlove product photo, Mattel, 1989.

PowerGlove product, Instructions, Mattel, 1989.

Crossan, Andrew, Williamson, John, Brewster, Stephen, A General Purpose Control-Based Trajectory Playback for Force-Feedback Systems, University of Glasgow, Dept. Computing Science, 4 pages.

Perry, Simon, "Nintendo to Launch Wireless Game Boy Adaptor," Digital Lifestyles, Sep. 26, 2003 http://digital-lifestyles.info/2003/09/26/nintendo-to-launch-wireless-game-boy-adaptor/.

Polhemus,"Fastrak, The Fast and Easy Digital Tracker" copyrighted 2001, Coldiester, Vermont, 2 pages.

Brownell, Richard, Review of Peripheral-GameCube-G3 Wireless Controller, GAF, Jul. 17, 2003, 2 pages.

Gyration, Inc., GyroRemote GP240-001 Professional Series, copyrighted 2003, www.gyration.com.

Holden, Maureen K., et al Use of Virtual Environments in Motor Learning and Rehabilitation Department of Brain and Cognitive Sciences, Handbook of Virtual Environments: Design, Implementation, and Applications chap 49, pp. 999-1026, Stanney (ed), Lawrence Erlbaum Associates 2002.

Nintendo"Kirby Tilt 'n' Tumble" video game, Nintendo, Apr. 11, 2001.

VTI, Mindflux-VTi CyberTouch, 1996, http://www.mindflux.com.au/products/vti/cybertouch.html.

Nintendo, Nintendo Entertainment System Consumer Information and Precautions Booklet, Nintendo of America, Inc. 1992.

Nintendo, Nintendo Entertainment System Instruction Manual, Nintendo of America, Inc. 1992.

Nintendo, Nintendo Entertainment System Booth 2002.

Nintendo, Nintendo Entertainment System Layout May 9, 2002.

Gamecubicle, Jim-New Contributor, Nintendo Wavebird Control, http://www.gamecubicle.com/news-nintendo_gamecube_wavebird_contoller.htm, May 14, 2002.

Nintendo, Nintendo Feature: History of Pokemon Part 2, Official Nintendo Magazine, May 17, 2009, http://www.officialnintendomagazine.co.uk/article.php?id=8576.

Philips, LPC2104/2105/2106 Single-chip 32 bit microcontrollers; 128 kB ISP/IAP Flash with 64 kB/32 kB/16 kB RAM Product Data, Rev. 05 Dec. 22, 2004.

Pokemon Pinball Game, 1999, Wikipedia Article, http://en.wikipedia.org/wiki/Pok?C3?A9mon_Pinball.

Satterfield, Shane, E3 2002: Nintendo announces new GameCube games, GameSpot, May 21, 2002, http://wwwgamespot.com/gamecube/action/rollorama/new.html?sid=2866974&com_act-convert&om_clk=nesfeatures&tag=newsfeatures%Btitle%3B.

Villoria, Gerald, Hands on Roll-O-Rama Game Cube, Game Spot, May 29, 2002, http://www.gamespot.com/gamecube/action/rollorama/news.html?sid=2868421&com_act=convert&om_clk=newsfeatures&tag=newsfeatures; title;1&m.

Wilson, Andrew and Shafer, Steven, Demonstration of XWand Interface for Intelligent Spaces, UIST '02 companion, 2 pages.

Wilson, Andy, "XWand: UI for Intelligent Environments", 5 pages. retrieved Jan. 11, 2009, http://research.microsft.com/en-us/um/people/awilson/wand/default.htm.

Hinkley et al, Proceedings for the working conference on Advanced visual interfaces, Portal: the guide to computing literature, 1 page, 2004.

Camarata et al., "Navigational Blocks: Navigating Information Space with Tangible Media," ACM 1-58113-459-2/02/0001, Jan. 13-16, 2002.

Zimmerman et al., "A hand gesture interface device", ACM-0-89791-213-6/87/0004/0189, 1987.

Kaplan, US S.I.R. H1383, Dec. 6, 1994.

Hinckley, Ken, "Synchronous Gestures for Multiple Persons and Computer," Chi Letter, vol. 5, Issue 2, pp. 149-158, ACM, 2003.

Toshiba, "Portege M200", Spec sheet, Nov. 2003, 2 pages.

* cited by examiner 1 kg

HUMAN MOVEMENT MEASUREMENT SYSTEM

This application is a continuation of U.S. Ser. No. 13/096,587, filed 28 Apr. 2011, which in turn is a continuation of U.S. Ser. No. 12/371,711, filed 16 Feb. 2009, now U.S. Pat. No. 7,952,483, issued 31 May 2011, which in turn is a continuation of U.S. Ser. No. 11/935,578 filed 6 Nov. 2007, now U.S. Pat. No. 7,492,268, issued 17 Feb. 2009, which in turn is a continuation of U.S. Ser. No. 11/187,373 filed 22 Jul. 2005, now U.S. Pat. No. 7,292,151, issued 6 Nov. 2007, which claims the benefit of U.S. 60/592,092, filed 29 Jul. 2004. Each of these is hereby incorporated by reference as if fully recited herein.

BACKGROUND OF THE ART AND SUMMARY OF THE INVENTION

This invention relates to a system and methods for setup and measuring the position and orientation (pose) of transponders. More specifically, for training the user to manipulate the pose of the transponders through a movement trajectory, while guided by interactive and sensory feedback means, for the purposes of functional movement assessment for exercise, and physical medicine and rehabilitation.

Known are commercial tracking and display systems that employ either singularly, or a hybrid fusion thereof, mechanical, inertial, acoustical or electromagnetic radiation sensors to determine a mobile object's position and orientation, referred to collectively as pose.

The various commercial tracking systems are broadly classified by their relative or absolute position tracking capability, in which system the pose of a mobile object is measured relative to a fixed coordinate system associated with either combination of receiver(s) or passive or active transmitter(s) housing mounted on the user. The tracking system's components may be tethered with obvious inherent movement restrictions, or use wireless communication means to remotely transmit and process the information and allow for greater mobility and range of movement.

Typically these tracking systems are utilized for biomechanics and gait analysis, motion capture, or performance animation and require the sensors to be precisely mounted on the joints. Various means of presenting the tracking information in a visual display are employed, such as Heads-Up Display (HUD), that provide occluded or see-through visibility of the physical world, or Fixed-Surface Display (FSD), such as computer desktop monitors, depending upon the simulation and immersive quality required for the application. The application may require various degrees of aural, visual, and tactile simulation fidelity and construct direct or composite camera views of the augmented or three dimensional (3D) virtual reality environment to elicit interactive user locomotion and/or object manipulation to enhance the user's performance and perception therein. The tracked object may be represented in the virtual environment in various forms, i.e., as a fully articulated anthropoid or depicted as a less complex graphical primitive. The rendering strategy employed depends upon the degree of photo realism required with consideration to its computational cost and the application's proprioception requirements.

Tracking technologies possess certain inherent strengths and limitations dependent upon technology, human factors, and environment that need consideration when discussing their performance metrics. Regardless of differentiating resolution and accuracy performance benchmarks, many implementations suffer from varying degrees of static and dynamic errors, including spatial distortion, jitter, stability, latency, or overshoot from prediction algorithms. Some human factors include perceptual stability and task performance transparency, which are more subjective in nature. And environmental issues such as line-of-sight, sensor attachment, range, and multiple-object recognition, need to be considered when selecting the optimal technology for the most robust application development. Irrespective of the intrinsic strengths and weaknesses of the tracking technology employed, ultimately the user's satisfaction with the system's utilization and efficacy, including the production of reliable, easily understood, measurable outcomes, will dictate the overall success of the device.

This invention's system and methods facilitates biomechanical tracking and analysis of functional movement. In the preferred embodiment, this invention is low cost, robust, easy to deploy, noninvasive, unobtrusive, and conveys intuitive and succinct information to the user to execute movement properly and provides performance indicators of said movement for feedback purposes. One feature of the present invention provides for an interactive tracking system because the sensor functionality, or referred to herein as active transponders or transponders, is integrated with local user input control, and real-time sensory interfaces on the same device. The transponder is a wireless communication and monitoring device that receives a specific signal and automatically responds with a specific reply. In one embodiment, the invention provides functional movement assessment based upon the relative measures of limb pose with respect to two positions defined by the transponders. The transponders can operate independently or work in unison to process and share computational tasks and information between the local databases. This decentralized, distributed processing scheme allows the configuration and coordination of the training session, and processing and analysis of the measurements to occur without requiring expensive auxiliary computer and display systems to manage the same, and without relying on costly software development of complex synthetic environments for visualization purposes. Also, the user can manage the applications and performance databases off-line on a remote computer system with Internet connectivity to customize and configure the system parameters in advance of their session.

The present invention is designed to provide such system and methods for high-fidelity tracking or registration of the poses of active transponders and engage the user to purposely manipulate the transponders' pose along a prescribed or choreographed movement trajectory in order to train and assess functional movement capability. In the preferred embodiment, the system is comprised of two subsystems: (1) a subsystem comprised of one or more active transponders, which, in its most sophisticated implementation, responds to periodic requests from another component of the system to radiate or transmit a signal for purposes of absolute position tracking; processes an embedded inertial sensor for relative orientation tracking and absolute tracking refinement; and provides an essentially real-time aural, visual, and tactile sensory interfaces to the user, and (2) a subsystem comprised of a centralized position processor system or unit and receiver constellation unit, collectively referred to as the processor unit, which is essentially a signal processor that synchronizes the transponders' periodicity of radiating signal and other operational states; collectively receives and processes the radiated signal; iteratively calculates the transponders instantaneous pose and convolution, thereof; and continually exchanges this information, and its' analysis thereof, with the transponders and/or auxiliary host computer system in essentially real-time via a combined wireless and tethered communication means. This real-time bi-directional exchange of information allows for proper transponder identification, coordination, and the accurate measurement of pose, thereof, and timely actuation of the sensory interfaces for optimal user regulated closed-loop control.

The transponder is broadly classified by its level of hardware and software configuration that define its scope of intelligence, sensory support, and configuration. The degree of intelligence is determined by its capability to locally access, process, and modify the database. Further, either transponder classification can be sub-classified by its manipulative requirements. In one embodiment, where multiple transponders are used, a principle transponder is consciously and deliberately moved along the reference movement trajectory, while a subordinate transponder serves as an anchor or secondary reference point elsewhere on the locomotion system whose kinematics are not necessarily controlled by the user's volition.

An interactive transponder, preferably, has significant intelligence; supports relative and absolute tracking capabilities; provides complete sensory stimuli support; provides for functional enhancement through attachment of modular, extension pieces; and provides a user display and input system to control the training session. In the preferred embodiment, the interactive transponder is primarily held in the hand to facilitate more complex user input and greater sensory intimacy. Conversely, in another embodiment, the fixed transponder has limited intelligence; supports only the absolute pose tracking capability; provides no sensory stimuli support; and is usually mounted to a fixed site on the limb or trunk.

A combination of transponder deployment strategies may be required depending on the training session's objectives, such as two interactive transponders grasped by each hand; or alternatively, an interactive transponder, and a fixed transponder attached to the limb or trunk; or lastly, two fixed transponders attached to the limb(s) and/or trunk.

In one embodiment, this invention proposes to elicit movement strategies based on the deployment of at least two transponders that define the endpoints of a movement vector whose relative translation and rotation is measured and evaluated for the assessment of functional movement capability, including but not limited to, limb range of motion and its control thereof, limb strength conditioning, and overall proprioception and hand-eye coordination skills, and overall body movement. This registration system measures a single movement vector whose endpoints are comprised of an anchor point, i.e. one that is located in a less dynamic frame of reference, e.g., such as the trunk or abdomen, and another more distal location fixed on or held by a limb or extremity, e.g., the hand, arm, or leg. As this movement vector is translated and rotated through space by the act of the user modifying the pose of the principle transponder in concert with the reference movement trajectory, the vector's length will expand and contract relative to the proximity of principle transponder with respect to the subordinate transponder. The vector's length conveys unique and explicit information regarding the user's movement efficiency and biomechanical leverage. For example, by attaching a fixed subordinate transponder at the hips and a fixed principle transponder on the upper arm, the biomechanics of the act of lifting a box or similar object can be elegantly qualified. If the user assumes a poor lifting technique, i.e. legs locked with the trunk severely flexed with head down and the arms stretched out beyond the basis of support, the vector's length would consistently be measured longer than compared to a good lifting technique, i.e., legs bent at knees with the back straight, head gaze up, and arms close to body. Also, the measurement(s) of higher-order derivatives derived from numerical mathematical processes of a reference point described by the vector would provide additional indication of movement control or smoothness. In summary, one embodiment of the present invention is comprised of:

a means to create a single movement vector whose endpoints are defined by the locations of at least two transponders, wherein, the expansion and contraction of the vector's length is calculated, analyzed, and reported in essentially real-time;

a means to create a single movement vector whose endpoints are defined by the locations of two transponders, wherein, a representative point along the vector length is referenced and its higher-order derivatives are computed by mathematical numerical processes, wherein the result is calculated, analyzed, and reported in essentially real-time; and, a means to correlate said vector's length and at least one other measure consisting of a higher-order derivative, to the reference movement trajectory, wherein the result is calculated, analyzed, and reported in essentially real-time.

A registration system for practical functional movement applications should clearly convey information to the user regarding his movement quality while he performs the task, without compromising or distracting from said execution by unnecessary head movements or change in eye gaze and normal focus. Poor visualization strategies that distract the user are ineffectual for promoting heads-up, immersive interaction, and the alphanumerical information it imparts often can not be consciously processed fast enough to elicit corrective action. This system provides for both a local, standalone sensory interface as a primary feedback aid, or alternatively, an interface to a remote fixed-surface display for greater visualization and simulation capabilities. The visual stimulus could be modulated to warn of range violations, or provide signals for purposes of movement cadence and directional cueing. A principle interactive transponder is typically handheld, which is naturally in close proximity to the user's aural and visual sensory field during most upper extremity movements, or, conversely, the visual stimulus may be viewed through a mirrored or reflective means if not in optimal line-of-sight. A remote fixed-surface display might augment the immersive quality of the user's experience by providing control of a view camera of a simulated computer environment, and display of the transponders and/or interactive objects' static or dynamic poses within the computer display's skewed through-the-window perspective projection.

In summary, one embodiment of the present invention is comprised of:

a means for modulating an embedded luminescent display organized and oriented into a directional-aiding pattern, by varying its degree of intensity and color, or other physical characteristics, to provide a visual display stimulus. This sensory interface is excited at a rate, repetition, or pattern proportional to the pose error of the transponders' movement trajectory compared to the reference movement trajectory;

a means to view said visual display stimulus with the aid of a mirror(s) or other reflective means;

a means for the real-time projection of sound or speech commands through an audio device to provide warning, alarm, instructional, and motivational aid, and/or additional cueing upon encroachment of static and dynamic limit/boundary conditions defined by the reference movement trajectory;

a means for real-time tactile feedback including, but not limited to, modulation of the rotational properties of a vibrator motor proportional to the pose error of the transponders' movement vector compared to the reference movement trajectory;

a means for combining the excitation of said stimuli proportional to the pose error of the transponders' movement vector compared to the reference movement trajectory; and, a means to coordinate the real-time, periodic parametric update and modulation of the stimuli imparted by the sensory interfaces within the transponders from a processing unit by means of a wireless communication link.

This invention addresses the need for an intuitive, interactive method to instruct, create, and deliver a movement trajectory command without necessarily relying on pre-programmed, regimented movement trajectories. The registration system can be configured via remote setup at the principle transponder to pre-record and choreograph a freeform movement trajectory of the principle transponder with the intent of the user mimicking the same said path. This impromptu learning modality can expedite the session down time between different users and movement scenarios, and accommodate users' high anthropometric variability in range of movement. In summary, one embodiment of the present invention is comprised of:

a means is to provide a movement trajectory learning modality that allows the user to calibrate and create the desired endpoints, midpoints, and/or total reference movement trajectory through user programmer entry of an input device resident on the transponder;

a means to process and save a movement trajectory using a computationally efficient Catmull-Rom spline algorithm or other similar path optimizing algorithms to create control points along key points of the movement trajectory that define the optimally smoothest path intersecting the control points;

a means to provide database management by a processing unit via a wireless communication link or, alternatively, through user data entry of an input device resident on the interactive transponder; and, a means to access, edit, and store the program and/or databases to nonvolatile memory operably coupled to the principle transponders for the purpose of automating the creation, delivery, storage, and processing of movement trajectories. Customized user programs and databases would be downloaded from a central repository or relevant website in advance of the training session to the transponder from the user's home location via the Internet or other convenient locales having networked Internet access, and transported to the systems remote physical location, and uploaded into the system's memory, and executed as the application program.

This a priori process of remote selection, download, and transfer of programmatic content and database would minimize the user's decision making and input during product utilization by offering only relevant and customized programming material of their choosing targeted for their specific exercise, fitness, or rehabilitation goals. Performance data could be saved indefinitely in the database's nonvolatile memory, until an upload process was performed through the said network so the database could be transferred to another location for purposes of, but not limited to, registration, processing, archival, and normative performance evaluation, etc.

An exemplary list of specific data structures contributing to or affecting the means for automating the creation, delivery, storage, and processing of movement trajectories described below may be stored within the non-volatile memory of the transponder or position processor which may use high-density serial FLASH, although other types of memory may be used such as SmartMedia, Compact Flash, etc. Additionally, the memory device interface should not be limited to internal, but may include external media devices, such as USB FLASH Key or other portable media means, that may have interoperability with other computerized devices. The data structures may include:

Modulation & Feedback Thresholds/Triggers Properties—the aural, visual, tactile interfaces require threshold settings which determine their excitation or stimulation characteristics. These settings can be derived from previous performance data or defaults determined from normative data, or modified in real-time, by algorithmic methods including moving averages, standard deviations, interpolation based upon goal-oriented objectives, etc.

Normative Performance—performance data collected over a large population of users through controlled studies, that is distilled down into specific user categories based upon certain demographics that the user may compare and rank his/her results. This data may be initially embedded within the transponders or position processor non-volatile memory and may be augmented or modified automatically or by user volition when connected to the Internet.

Competitive Ranking—applications which have a predominate point goal-oriented purpose would allow access to a global ranking file archive accessed through the Internet or automatically via updated executive files. This ranking file would be created through an analysis of user participation and publishing of his/her results through Internet Web-based services.

Downloadable Executive Programs & Configurations—new software programs, including new features, enhancements, bug fixes, adjustments, etc., could be downloaded to the transponder through an Internet connection. Graphics images would be stored in compressed or uncompressed binary forms, i.e., bitmap, gif, jpeg, etc. These new programs could be transferred to any suitable computerized position processor unit located at a remote facility via the transponder's wireless link. Therefore, the user's transponder is the node that establishes the portable network, capabilities of the system, not necessarily the computerized position processor.

Custom Menu Interfaces—specialized activities may require more advanced (or simplified) interfaces dependent upon the users' cognitive abilities and interactive specificity. This menu may include interactive queries or solicit information regarding, the user's daily goals, subjective opinions or overall impression of the activity and ones performance which could be incorporated in the Motivation Index described below.

Report Generation Tools and Templates—XML, HTML or other authoring language used to create documents on the Web that would provide an interactive browser-based user interface to access additional performance data analysis and report generation tools and templates that may not be available or offered with the standard product.

Custom Performance Algorithms—certain application-specific performance analysis may require dynamically linked algorithms that process and calculate non-standard or specialized information, values, units, physical measurements, statistical results, predictive behaviors, filtering, numerical analysis including differentiation and integration, convolution and correlation, linear algebraic matrices operations to compute data pose and scaling transformation, and proprietary types. One example of a proprietary type is Motivation Index, a composite numerical value derived from a weighted average of statistical performance indicators and subjective user input including relative scoring improvements, conformity to ROM pattern, lengthy activity access duration, high access rate, relative skill level improvement, daily goal achievement, etc., that could represent the overall level of enthusiasm and satisfaction, the user has for a particular activity.

Range of Motion (ROM) Pattern Generator—the ROM pattern requires some key control points to be captured along the desired trajectory and stored in order that the algorithm can calculate an optimally smooth path, in real-time, during the comparative analysis phase.

ROM Pattern Capture & Replay—the ROM pattern can be saved to memory in real-time by discrete position samples versus time depending upon the resolution desired and memory limitations and later played back on the transponder or remote display for analysis.

Activity Specific Attributes—includes Reps/Sets, Duration, Pause, Heart Rate Limits, intra-activity delay, level, point scalars, energy expenditure, task-oriented triggers, etc., and other parametric data that controls intensity, execution rate and scoring criteria for the activity.

Instructional Information—textual, graphical, or animation-based instruction, advice, coaching, activity description, diagramed transponder deployment and intra-device connectivity, etc. that facilitates the intuitiveness, understanding, and usage of the system. The form of instruction may include music files saved in various formats, including Wave, MP3 or other current or future audio data compression formats, and video files saved in MPEG or other current or future video data compression formats.

Real-time Data Management—proprietary data management protocols that reside above the communication driver layer that manage the real-time, synchronous and asynchronous exchange of data between transponder(s) and position processor. This would provide an essential real-time sharing of activity data, analysis, and feedback stimulus thresholds, or coordination of multiple transponder configurations, or for a collaboration of same or different user requirements to complete a similar activity objective.

This invention addresses the need for adaptability of the registration system to different movement measurement scenarios. In one embodiment, it utilizes a versatile, modular configuration and mounting of the transponders onto the user. The efficient deployment of the transducers between different users' and from task to task requires a universal mounting scheme to provide consistent localization and pose of the transponders at the desired measurement sites on user's body. Also, to compensate for the receivers' finite tracking volume when stationary, the receiver constellation unit may be mechanically modified to optimize its tracking properties by conveniently repositioning it in closer proximity to the expected transponders movement trajectories and line-of-sight, thereof. In summary, one embodiment of the present invention is comprised of:

a means to quickly and efficiently alter the location of the transponders using a fastening system designed to quickly attach and dispose various forms of transponder assemblies;

a means to augment the physical properties, i.e., weight and length, of the principle transponder with adjunct electro-mechanical components that provide variations in biomechanical leverage for isotonic and isometric utilization; and, a means to allow the user to manually alter the geometry and pose of the receiver constellation unit to facilitate an optimal tracking location based upon collectively maximizing the ultrasonic source's energy received at the transducer interface.

This invention addresses the practicality and robustness of the registration system when used in either indoor or outdoor environments, and especially when the tracking volume likely contains potentially occluding objects, i.e., uninvolved limbs or clothing, that become potential sources of competing, reflected paths. The preferred embodiment of the registration system utilizes the time of flight (TOF) measurement of ultrasonic acoustic waves due to its immunity from interference from the visible and near-visible electromagnetic spectrum and its superior ability to overcome most multi-path reflections problems by simple gated timing of the initial wave front. Upon command from the processor unit, the transponders produce a few cycles burst of ultrasonic energy and the transducers of the receiver constellation unit are stimulated and mechanically resonate accordingly, upon the wave front arrival. The processor unit's analog signal processing circuits transform the mechanical energy into electrical signals that resemble tapered sinusoidal waveforms, which another electronic circuit triggers upon using an adaptive threshold technique which, in turn, the processor unit detects and calculates TOF timestamps indicating the wave front arrival. In the preferred embodiment, the system overcomes the ultrasonic technology's intrinsic challenge of precisely triggering on the same waveform location and provides consistent unambiguous trigger detection by complementing the adaptive threshold technique with a software timestamp correction algorithm, which includes in part, a digital over-sampling and averaging timestamp algorithm, a relative timestamp correction scheme utilizing a predictive algorithm of higher-order Taylor series based derivatives, and an absolute timestamp correction scheme that minimizes the range error based upon discrete biasing of timestamps.

Further, in the preferred embodiment, the processor unit utilizes the absolute and relative trigger timestamps in a multi-modal trilateration algorithm for the measurement of three-dimensional (3D) translations and rotations of the transponders. The primary trilateration calculation is derived by an application of Pythagoream theorem involving a point position solution based-upon range measurements from at least three (3) points, versus the well-known triangulation method which uses bearing angles of two cameras of known pose. Additionally, the system's main accuracy limitation is mostly affected by the temperature variability of outdoor environments and its influence on the speed of sound in air value. This algorithm mitigates this problem by mathematically computing the speed of sound every analysis period provided at least five (5) receivers and a transponder synchronizing means are utilized. If the integrity of the synchronizing signal is temporarily compromised, the system automatically employs a variation of the trilateration algorithm that uses the last known speed of sound value.

In the preferred embodiment, the maximum update rate, and hence the major contributor to the latency of the position calculation, is determined by the typical acoustical reverberation, typically between 20 to 100 ms, encountered in an indoor environment. Since the transponders are held or fixed on the user's body and, therefore, are mobile, the TOF measurements will experience an additional latency effect. A Kalman filter is used as a prediction/estimation strategy to minimize and compensate for the latency effect. The prediction algorithm uses a higher-order Taylor series based derivatives and augmentative inertial sensor data. Its predictive refinement is dependent upon predefined models of expected movement conditions. Because functional movement is episodic, having periods of stillness interspersed with bursts of motion activity, a Multi-modal filtering strategy is preferably employed to handle the unpredictable jerkiness at the start of motion and relatively predictable, smooth motion afterwards. In summary, the preferred embodiment of the present invention is comprised of:

a means to detect the same carrier wave cycle of ultrasonic energy using a software correction algorithm requiring multiple, consecutive TOF acquisitions as input for the digital over-sampling and averaging algorithm, the calculation of a higher-order numerical differentiation of the past and current TOF information as input for the predictive algorithm of higher-order Taylor series based derivatives used for the relative TOF correction, and a measurement of the intra-pulse time intervals of consecutive TOF acquisitions as input for the absolute TOF correction scheme that minimizes the range error based upon selective biasing of the TOFs;

a means to utilize a dual matrix formulation of the trilateration algorithm, and a calculation strategy thereof, which decision is dependent upon the integrity of the system's communication link, synchronization condition, and the desired measurement accuracy; and, a means to coordinate the information transfer between transponders and the processor unit so that their contribution to the resultant movement vector calculation can be measured without intra-signal interference.

These goals will be attained by such system and methods that are comprised of the user's interaction described by the following steps as set forth as the preferred embodiment:

a. Authenticate user access and open user session from a local or remote database;
b. Setup user training session, i.e., workload limitations, measurement criteria, and audio/visual/tactile stimuli;
c. Select training program and configure its options;
d. Deploy the transponders as instructed to predefined locations of users locomotion system to create at least one transponder movement vector;
e. Calibrate the transponder movement vector to establish its reference pose;
f. Create a movement trajectory using learn mode, if required;
g. Initiate the start of session;
h. Determine the instantaneous pose of transponder movement vector relative to its reference pose from a periodic temporal iteration of this step;
i. Perform qualitative and quantitative statistical analysis of accumulated measured poses of the transponder movement vector relative to the pattern of instantaneous poses defined by the reference movement trajectory;
j. Update the major transponders sensory interfaces to modulate said system parameters in a periodic temporal iteration of this step;
k. End the session once program objectives have been obtained;
l. Analyze the results by interacting with local and/or remote databases;
m. Provide numerical, graphical, and/or animated information indicating desired performance measurements.

BRIEF DESCRIPTION OF THE DRAWINGS

The disclosed embodiments will be better understood when reference is made to the accompanying drawings, wherein identical parts are identified with identical reference numbers and wherein.

DETAILED DESCRIPTION OF THE EMBODIMENTS

Figure 1A:
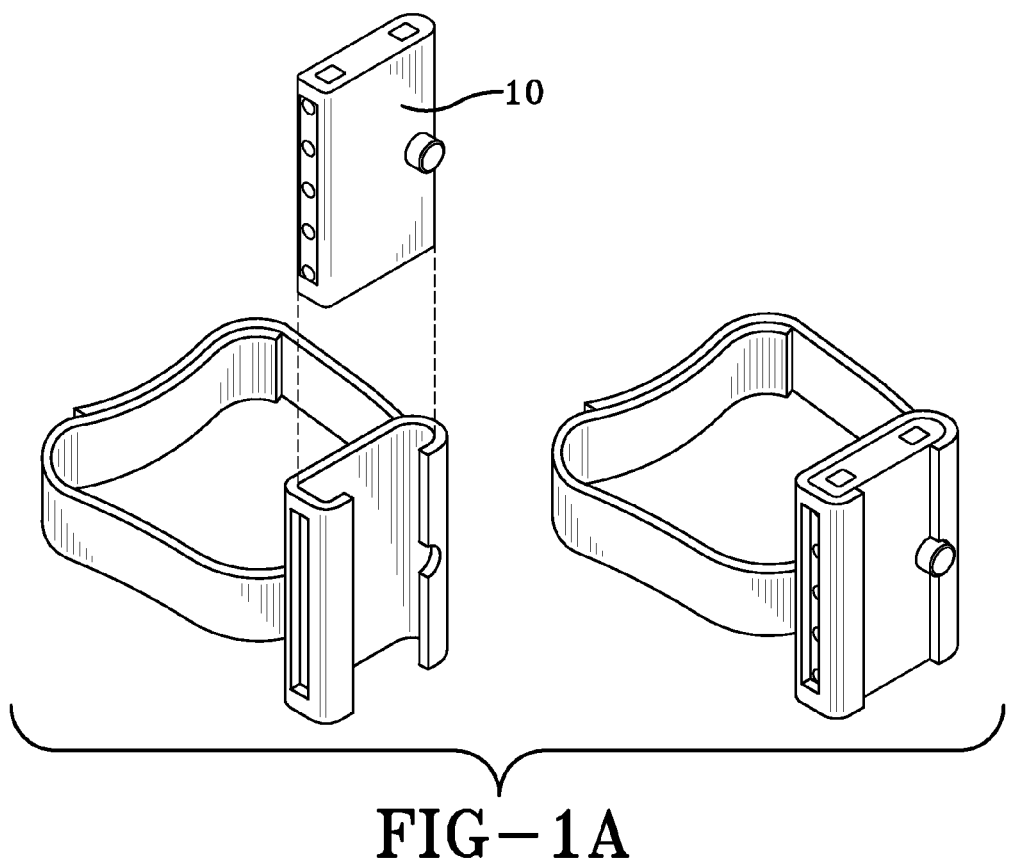
FIG. 1A illustrates one example of a deployment apparatus of the present invention.

The present invention provides a practical, versatile measurement tool for the assessment of the user's manipulation strategy of the transponder 10 or transponders along a reference movement trajectory. Moreover, the system and methods measure and analyze the kinematics of the relative translations and rotations of the limbs or extremities with respect to each other or to a more inertial reference location on or off body as the transponders are manipulated. This information provides useful insight on biomechanical demands and anthropometric factors that influence human movement efficiency and control. Although measurement performance metrics are important design criteria, it's equally important to provide intuitive and motivating program instruction and administration, and to provide comprehensive analysis and integration of the motion data in a form that is objective and easily interpreted. This system improves upon the practicality and user interactive aspects of setup, deployment, calibration, execution, feedback, and data interpretation of a tracking system designed for function human movement.

Human movement is a response to external environmental forces which requires the accurate coordination of the distal segment(s) to compensate for these forces. Skillful coordination of human movement is dependent upon the cohesive interaction of multiple sensory systems, including visual, vestibular, with the musculoskeletal system. More specifically, the challenges and goals of (1) cognitive spatial mapping, (2) minimization of energy expenditure, (3) maintaining stability, (4) steering and accommodation strategies for various environments, (5) dynamic equilibrium, (6) active propulsion and weight support, and (7) core locomotion pattern should be relationally considered to properly assess human movement. Therefore, it is preferable to engage the interaction of these sensory systems during a training session to promote the desired functional movement outcome. Because many movements persist for 400-500 ms, enough time is allowed for the initiation of the movement and for user correction based upon visual and kinesthetic information acquired during the time of the movement. However, the implemented means of visual feedback should be not be distracting or interfering with the task at hand. In the preferred embodiment, this system engages the sensory systems with non-distracting, intuitive, embedded aural, visual, and tactile stimuli which provide real-time indication of the principle transponder pose error with respect to the reference movement trajectory.

In order to conduct a time efficient training session, this registration system attempts to minimize the encumbering experimental setup and calibration procedures characteristic of more complex and higher cost motion analysis technology. These complementary systems serve important academic or clinical oriented research needs or for motion capture for computer animation purposes and strive for highly accurate measurement of joint motion data in terms of angular displacement. Therefore, the integrity and reliability of their motion data is dependent upon proper sensor setup and calibration.

For instance, single axis goniometer-based systems usually require specially designed harnesses to hold the monitor and are firmly strapped or taped over the joint to avoid relative motion artifacts. Usually these devices are tethered and their fit, weight, and constraining mechanical linkages can impose limitations on the joint motion and cause discomfort for the user. Most optical or video-based systems require the placement of numerous active or passive markers over landmarks, such as the joints' center of rotation. These systems should guarantee sufficient environmental illumination and contrast between markers and background to function optimally. Also, these systems are severely affected by occluded markers that may disappear for long periods of time due to rotations and line-of-sight limitations. Other video-based systems do not use markers but require the assignment of the body's joints manually or through computerized automation during data analysis, making real-time analysis arduous and real-time feedback virtually impossible.

In the preferred embodiment, the system doesn't require complicated, time consuming sensor setup and calibration by virtue of its minimalist sensor requirements and uncomplicated sensor mounting. Instead, it requires only the deployment of a sensor on the body (in one embodiment a dual sensor group on a combination of limb(s) and or trunk) and doesn't enforce stringent movement protocol, but encourages free-form, unrestrictive movement of the transponders.

Figure 1B:
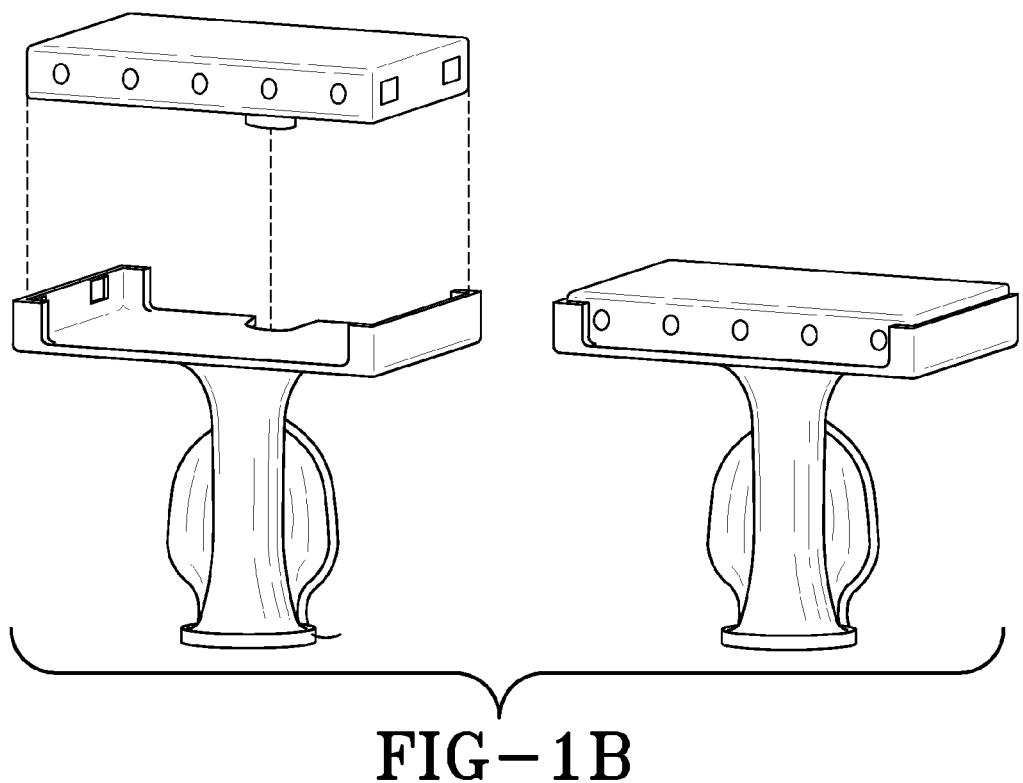
FIG. 1B illustrates one example of hand-held form for the transponder of the present invention.
Figure 2A:
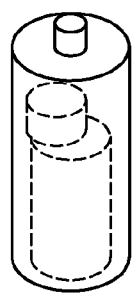
FIGS. 2A-2D illustrate example extension pieces for the present invention.
Figure 2B:
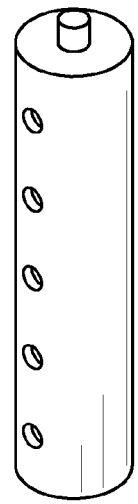
Figure 2C:
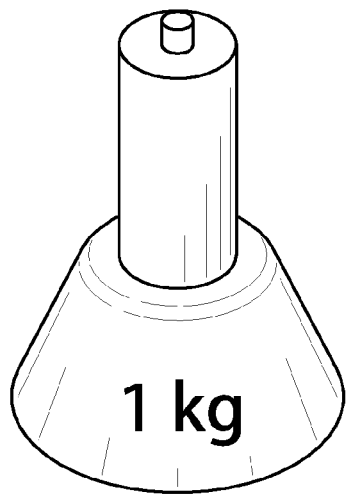
Figure 2D:
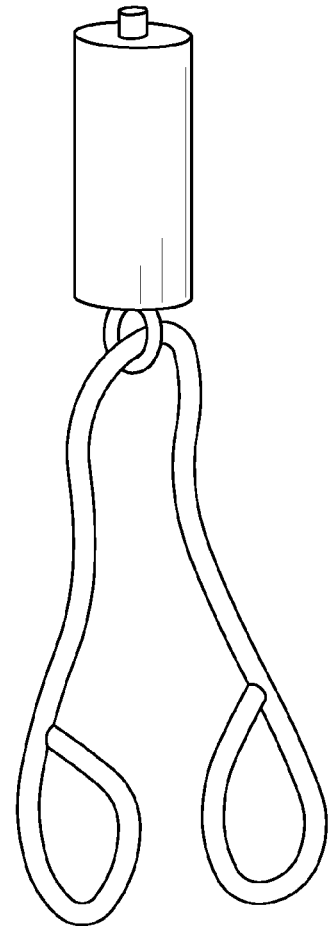
Figure 3A:
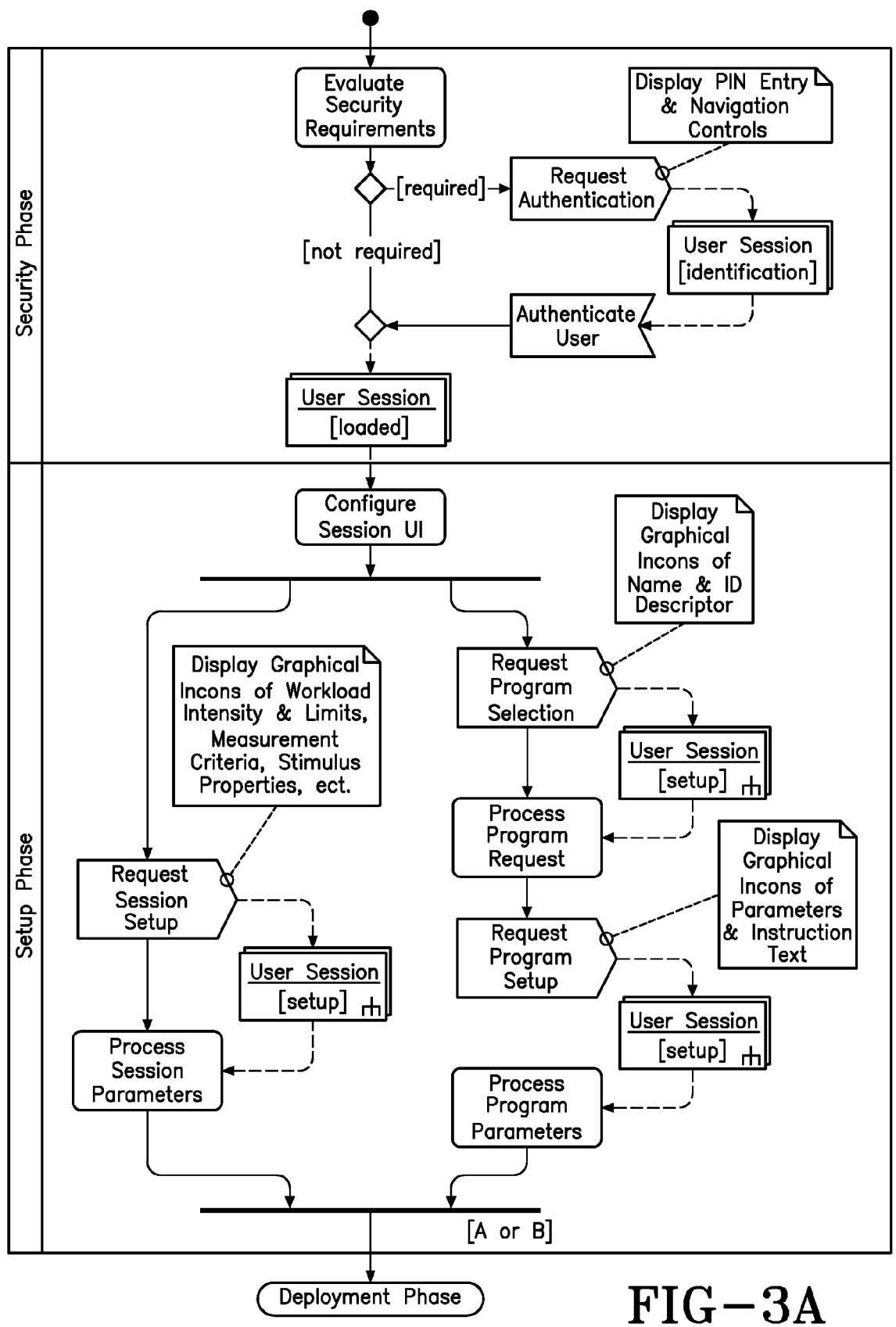
FIGS. 3A-3D illustrate one example of process flows for the present invention.
Figure 3B:
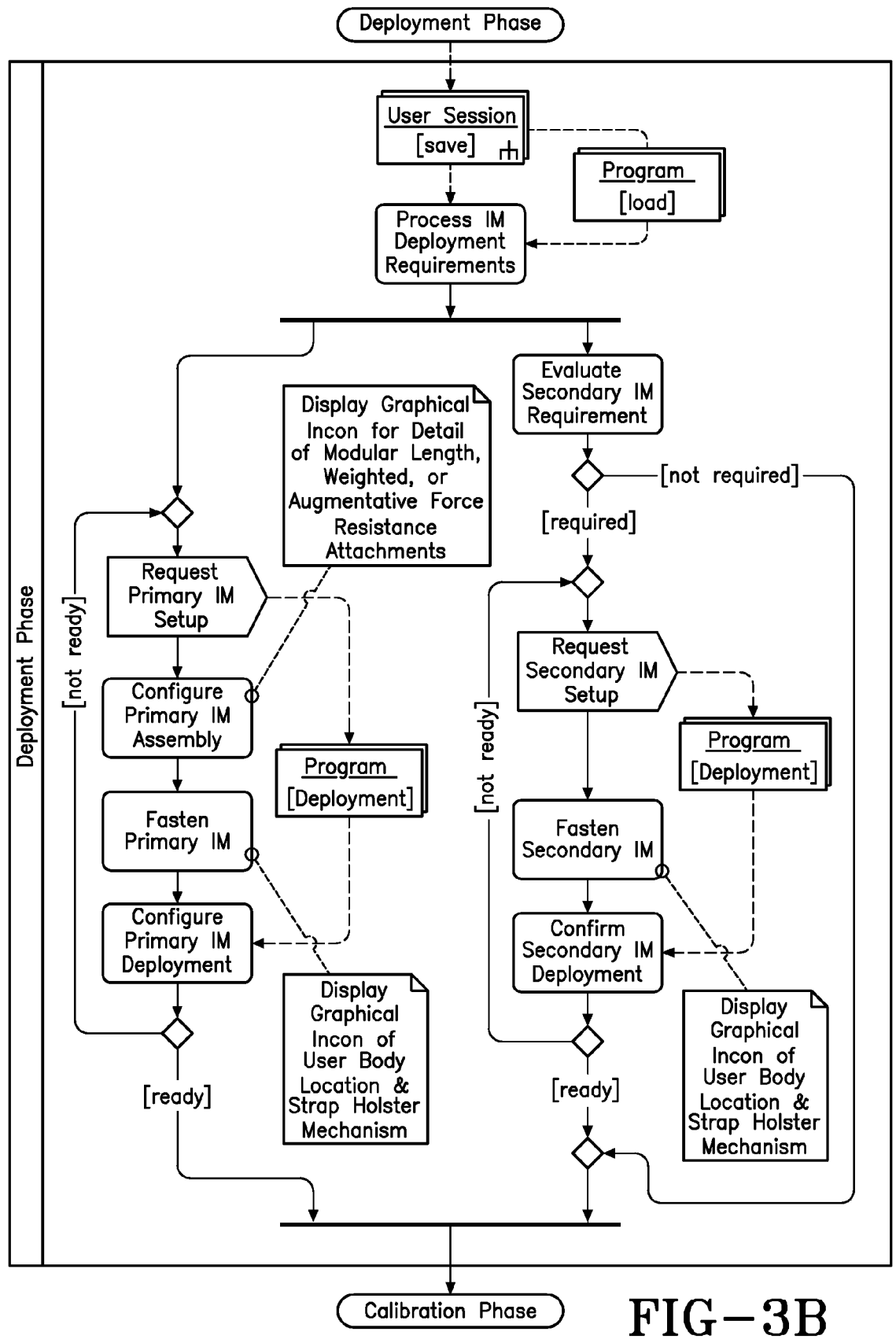
Figure 3C:
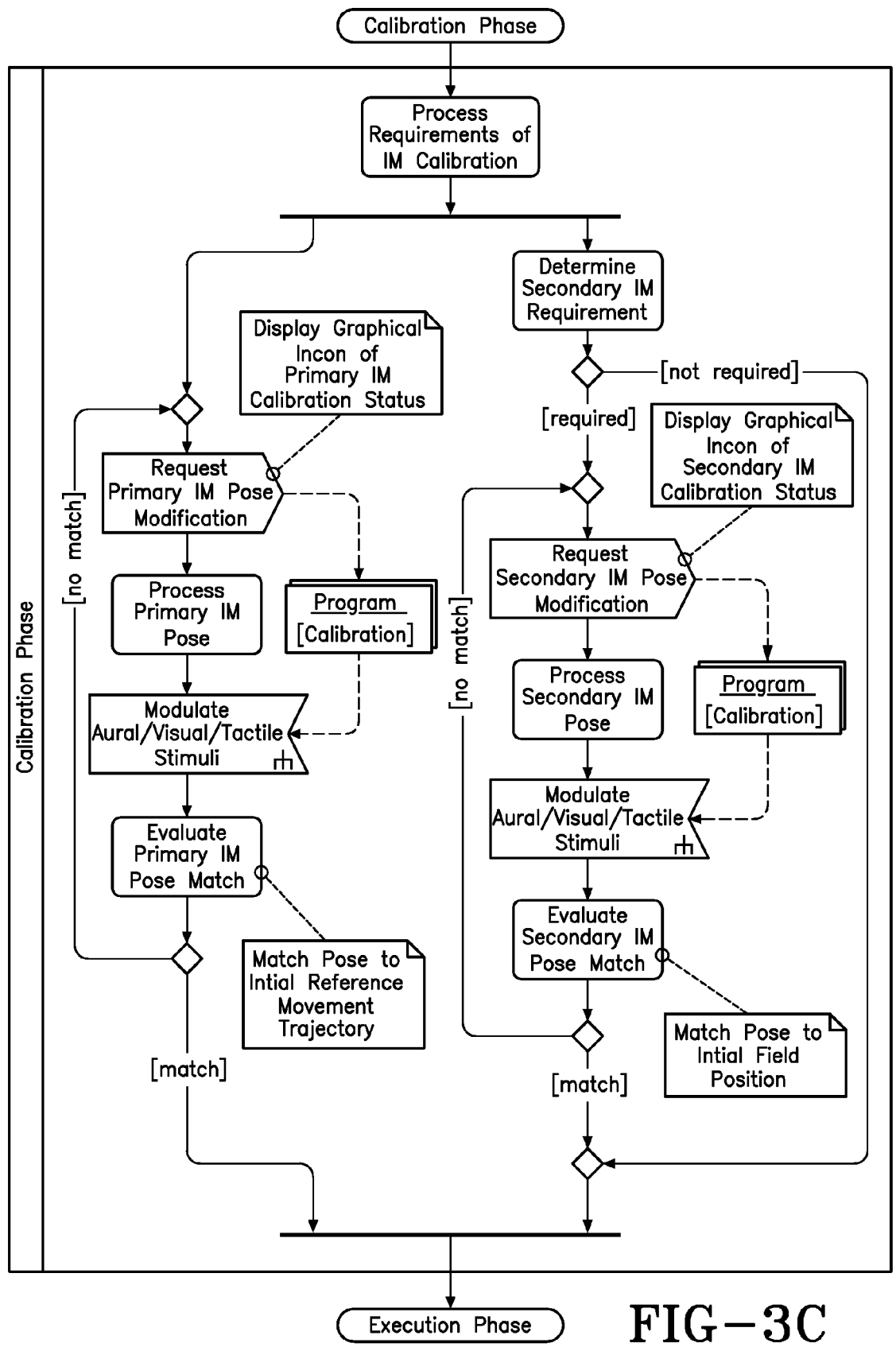
Figure 3D:
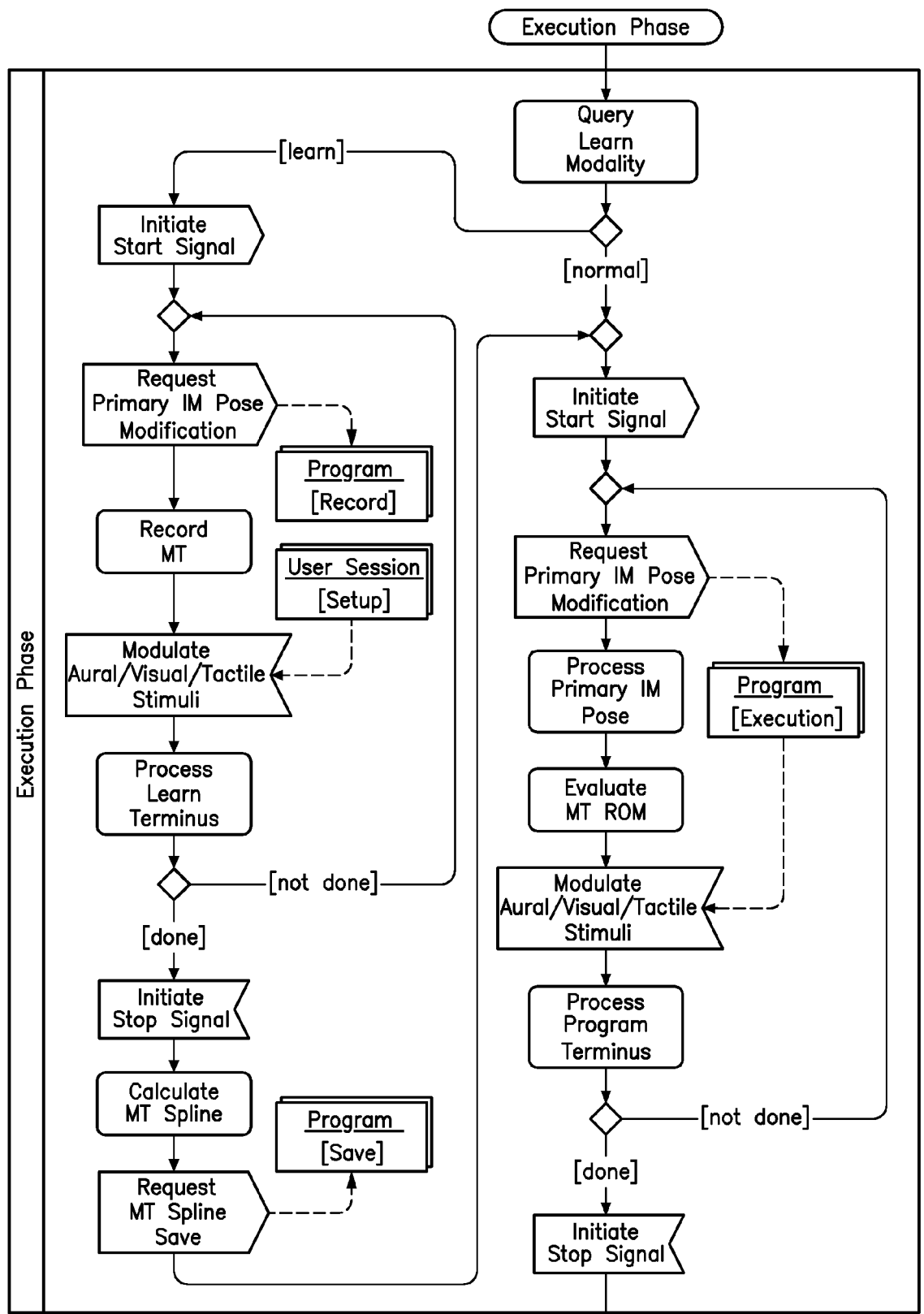

The transponder's preferred deployment means, include either insertion into a universal strap and holster apparatus (FIG. 1A) that secures on the user's limb, extremity, or trunk, including, but not limited to, the hip, ankle, knee, wrist, upper arm, neck, waist or an augmentative mechanical attachment to one or a combination of modular extension pieces shaped into a hand-held form (FIG. 1B). A strap or torx-like clip and holster design provides a firm, yet light weight and comfortable mounting location away from areas that clothing and/or uninvolved limbs may occlude.

The modular extension piece is either an instrumented sensory type designed to support alternative tactile stimulus device or alternative configurations of aural, visual, and tactile feedback types, or non-instrumented, weighted extension pieces as shown in FIGS. 2A-2D. All modular extension pieces may be of various physical dimensions and intrinsic weight, with a captive handle design that preferably requires zero grip strength to grasp. Alternatively, the modular extension piece may be coupled to the transponder, through a fixed or flexible, segmented, articulated coupling to accommodate attachment of additional transponders and/or other modular extension pieces. These components would quickly assemble to each other using a spherical snap joint or twist snap latch, or similar mechanism, to provide quick alteration of form and function when used for different movement trajectory scenarios.

In one embodiment, the weighted extension attachments (FIG. 2A) are offered in fixed gradations of one (1) kilogram increments or other convenient unit of measure and either be indicated as such with a numerical label, quantitative mark, or color-code feature, or combination thereof. For upper extremity evaluation, the weighted extension piece integrated into a zero-grip handle would enhance the improvement of musculature strength of the limb, while not compromising the user's endurance with a potentially fatiguing hand grasp requirement.

In one embodiment (FIG. 2B), the tactile type provides force feedback functionality by controlling the rotational speed of an embedded vibrator motor in the shaft. Alternatively, the visual type (FIG. 2C) may be comprised of a series of light emitting diodes that could be uniformly embedded along the length of the handle or transponder and their intensities variably controlled therein. It should be appreciated that a simple, economical mirrored or reflective surface placed in front of the user's visual field could provide sufficient real-time indication of the user's subjective conformity to the said movement trajectory while allowing non-distracting viewing of this visual stimulus. For example, a program that requires the user to reposition the principle interactive transponder through an arc-like movement trajectory in the midsagittal plane through out a range of motion beginning from the waist upwards until parallel to shoulder height. As the user performs the movement, the visual sensory interface could be proportionally excited if the user moves too quickly, or hesitates too long, or produces shaky or erratic episodic motions, or is beyond the prescribed bounds of the movement arc. The light stimulus is easily viewed in the mirror and would indicate corrective action in his or her movement strategy, while appropriate aural commands may be issued simultaneously to encourage the same correction. Regardless of the sensory interface type, its control and excitation properties will be determined by some statistical aspect of the user's conformity to and progression through the movement trajectory.

The hand-held transponder may include a modular extension piece with an embedded graphic display device and associated input means to allow the user to setup, operate, provide visual feedback, and view performance results of the device usage without additional remote display means. More specifically, a software-controlled user interface could provide certain visual prompts in a menu oriented presentation, to instruct the user on (1) device setup, i.e., aural, visual, and tactile feedback parameters, types of program start and termination cues, program intensity based on ratio of amount of repetitions, sets, and rest periods or categorical gradation of challenge, learn mode behavior, etc., (2) scrollable program selection with brief descriptions including objective, desired measurement, i.e., range of motion, energy, accuracy, speed, etc., and instructive information, and (3) alphanumeric and/or graphical display of measured performance data and other biophysical data and its analysis thereof, displayed in standard plotted forms including line, bar, and pie charts, etc. It is important to note that the user input process is intuitive and streamlined so as not to detract from the practicality and user friendliness of the system. Only relevant applications and its control thereof will be sequestered from the database and presented to the user.

In one embodiment, two or more transponders and extension pieces, or combinations thereof, may be assembled at their endpoints with a universal spring coupling. The assembled device could be grasped in both hands and bent in various rotational angles about the spring coupling's axis. Isotonic strength conditioning programs can be developed due to the force resistance feedback supplied by the spring. A multi-transponder assembly in the form of a flexible rod or staff could provide an indication of balance of upper extremity strength and proprioceptive function dependent upon the angular closure rate and rotational imbalance and orientation deviation from initial starting position.

Additionally, in the preferred embodiment, the modular extension pieces have provisions for other attachable apparatus (FIG. 2D) that can augment the program's intensity or difficulty. For example, an eyelet is embedded in the end of the extension piece and is designed to attach an elastomeric band, such as the type manufactured by Theraband®. By securing the other open stirrup end of the band to the user's foot, isotonic strength conditioning programs can be developed due to the force resistance feedback supplied by the elastomeric band. Moving the transponder through a movement trajectory is now made more restrictive and challenging.

APPLICATION EXAMPLES

An example training session deploying a dual transponder group is now described that may be designed to improve the range of motion, strength, and coordination of shoulder abduction in a user. The training session would primarily serve as an exercise aid that provides essential feedback to the user so that he/she learns to progressively improve the manipulation of the transponder through the reference movement trajectory, while benefiting from increased shoulder range of motion and strength improvement.

In advance of the training session, a software application is operated from a host computer that provides a utility for baseline configuration and management of the system's and transponder's local databases, and/or access to other remote databases, and for the real-time interface to the data flow between the system's components. The application's navigation and selections are presented to the user through a typical graphical user interface like Microsoft Windows® XP operating system. A generalized step-wise procedure requires the administrator or user to (1) select the desired program and features from a menu screen list, and (2) to initiate a communication process that causes the program parameters to be transferred to the processor unit through a standard computer communication protocol, i.e. serial, USB, ethernet, etc., whereupon, (3) the information is subsequently processed and transferred into the transponders local memory via a wireless communication link, and, finally, (4) the transponder's software program accesses this database to manage the device utilization and configuration of the local display means. Alternatively, a Compact FLASH-based memory card, embedded serial FLASH, or a similar nonvolatile memory device provides the user an additional specialized database supporting remote data collection capabilities. This database would be preprogrammed in advance and the resultant performance data retained, even if the device's power is lost, or for extended unsupervised exercise sessions conducted remotely from the host computer system or when the host computer system is unattached or unavailable. After the session is completed, the user would be queried if the results are to be saved for later analysis or would automatically be saved, dependent upon device setup. This data could be retrieved at a later time when the system is once again attached to a host computer system, and the software utility could be commanded to upload the database.

Henceforth, the following procedural description refers to the activity dependencies diagrammed in FIGS. 3A-3D that the user would encounter while operating the system.

During the Security Phase (FIG. 3A), the user may be requested to provide a security authentication code for validation, which opens access to his/hers custom programs in the training session. Next, during the Setup Phase (FIG. 3A), the user can configure global options or select the desired program. The global options may include, but are not limited to, workload intensity, measurement criteria, sensory interface properties, and reporting features. A program menu list would indicate name, ID, and a brief description, or alternatively, be represented by a detailed graphical icon. When the program is selected, other program-specific options can be setup.

Figure 4A:
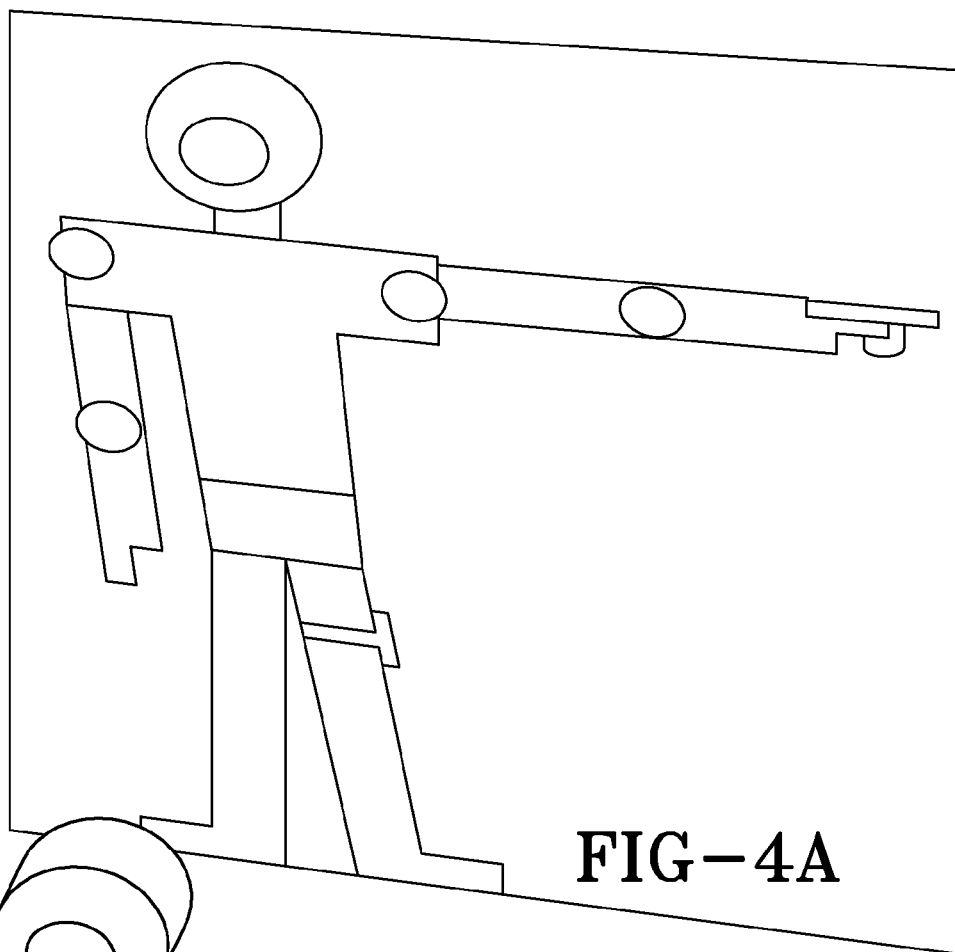
FIGS. 4A and 4B illustrate a sample application of the present invention.

During the Deployment Phase (FIG. 3B), and dependent upon the program's objectives, a suitable combination of transponder types will be mounted on the user's body as instructed by the program. This example requires the assembly of a hand-held interactive transponder with graphical display, and a weighted extension piece coupled therein to be grasped by the hand on the same side as the affected shoulder. Another subordinate transponder 12 is placed into a holster assembly strapped around the lower quadriceps on the same side. This setup is shown in FIG. 4.

During the Calibration Phase (FIG. 3C), a simple calibration procedure may be requested to evaluate transponder function and specific user range of motion constraints. Typically, this information is determined beforehand and saved in the system's database. Also, practicality of this system is claimed for lack of extensive calibration requirements.

Figure 4B:
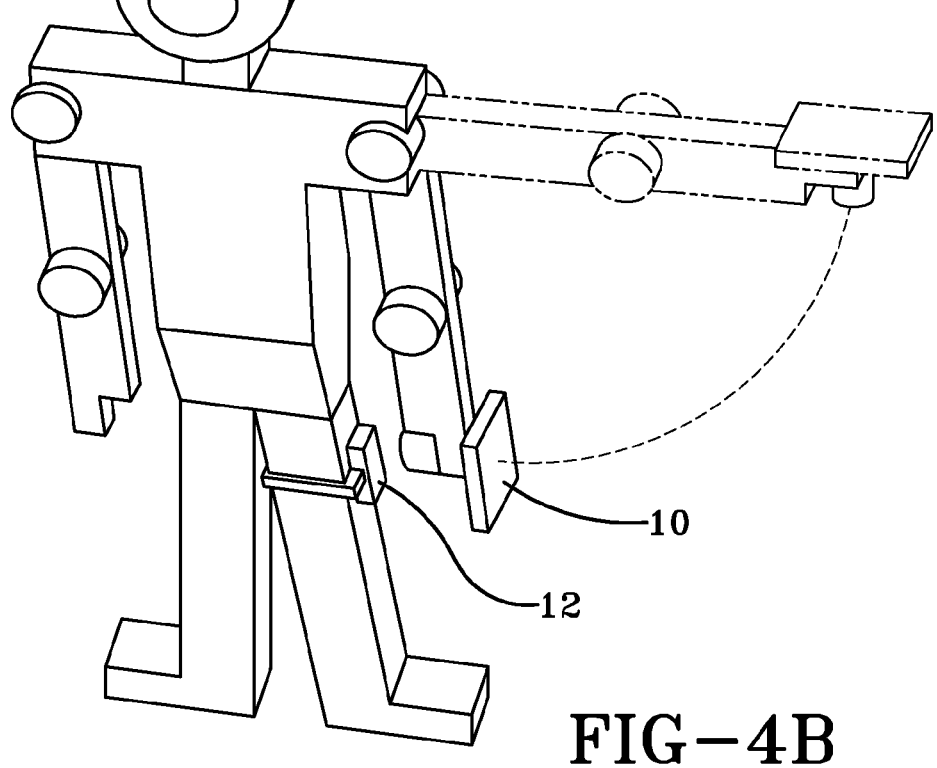

Dependent upon the program's options, a user-defined movement trajectory may be created prior to program start in lieu of executing the predefined version. The learn mode could be utilized to quickly choreograph free-form movement trajectories and save them into the transponder's nonvolatile memory for later execution. The learn mode would be accessed through the user interface and instruct the management of the control point assignment by pressing the push button switch at the appropriate junctures of movement discontinuity or, preferably, allowing automated assignment by the software. In the preferred embodiment, a computationally efficient Catmull-Rom spline is used to define a three dimensional (3D) curve that passes through all the control points along the movement trajectory path. If manually interceding, the user is instructed to press the push button once at each major juncture in the movement trajectory, but, preferably, for no more than a few locations, until the desired end of range of motion is reached as shown in FIG. 4B. Similarly, the return path may be similarly defined or he/she may elect to use the same forward path in reverse. These control points are registered by the processor unit and transferred and saved to the transponders' memory to serve as the control points for the real-time calculation of a Catmull-Rom spline. The Catmull-Rom spline is calculated in real-time from the desired initial starting point to provide a continuous set of position points representing the "learned" reference movement trajectory.

After the program is selected or the learn mode complete, the user may be instructed to alter the pose of the transponders to satisfy the initial starting conditions of the program. Either one or a combination of sensory interfaces could be excited by the principle transponder to cause the user to direct or steer it towards the desired start point. For instance, the visual sensory interface could sequentially extinguish or dim its peripheral light sources to converge to a central light source as the principle transponder is positioned closer to the desired start point. Alternatively, the aural sensory interface could change its tonality and loudness as the start point is approached. Or alternatively, the tactile sensory interface could be modulated to provide less force feedback as the start point is approached.

During the Execution Phase (FIG. 3D), the transponders are continually manipulated along the reference movement trajectory to the best of the user's skill and fidelity, within the bounds of the user's physical limitation, until an aural, visual, or tactile response is given that indicates the activity volume has been successfully completed or a sufficient number of conformity, violations or failures have been registered. The processor unit calculates the instantaneous pose coordinates of the transponders every analysis interval and periodically communicates this information to the transponders via the wireless communication link. As the principle transponder is moved in mimicry to the reference movement trajectory the conformity error between the actual and reference movement trajectory is calculated periodically in real-time to determine the characteristics of feedback quality to be elicited by the sensory interfaces for the user's closed-loop control to correct his/her manipulation strategy. For example, the conformity error may be calculated from statistical processes based upon the standard deviation of the least mean squared (LSM) principle transponder's position error compared to the reference movement trajectory, or based upon, or combination thereof, a threshold magnitude of some multi-order numerical differentiation of said movement to indicate a "smoothness" quality of translation and rotation along the movement trajectory path.

Alternatively, a host computer system could provide an auxiliary processing and display means to allow another software program to access the transponder's calculated positional data through an application programmer's interface and use this data to alter the pose of a graphical primitive in proportion to the motions of the transponders within the context of computer generated virtual environment. The dynamic control of objects in the computer generated virtual environment could be used to augment the local sensory interfaces of the transponders through an interactive, goal-oriented video game modality. The video game challenges could be increased over time based upon some scoring criteria of successful manipulation of the principally controlled on-screen graphical object with respect to cueing derived from other secondary static or dynamically moving objects. It is important to note that only primitive forms of video game challenges would be considered, to take into account the user's cognitive awareness and physical limitations, and the economics of software development for photo realistic virtual environments and animation. Also, this auxiliary computer display means would offer an alternative visualization method of interactive and immersive video feedback aid to enhance the application presentation.

Additional examples of how the present invention may be applied are described as follows:

Balance

The body has the ability to maintain balance under both static and dynamic conditions. In static conditions, such as in standing, the body strives to efficiently maintain posture (often referred to as postural stability) with minimal movement. In dynamic conditions such as in walking or sports play, the body strives to maintain balance while performing in an ever changing environment. The ability to maintain balance is a complex process that depends on three major sensory components. The sensory systems include visual, vestibular and proprioception. For example, we rely on our visual system (eyes) to tell us if the environment around us is moving or still; we rely on our vestibular system (inner ears) to tell us if we are upright or leaning, standing still or moving; and we rely on our proprioceptive system (feet and joints) to tell us if the surface we are standing on is uneven or moving. If balance problems develop, they can cause profound disruptions in your daily life. In addition to increased risk for falls, balance disorders can shorten attention span, disrupt normal sleep patterns, cause excessive fatigue, increase dependence on others and reduce quality of life. It is not uncommon for individuals with a history of balance problems to regain their balance control through accurate diagnosis followed by specific medical treatment and/or rehabilitation exercises.

The present invention described can be used as a testing and training device for balance improvement under both static and dynamic conditions.

One testing and training scenario for postural stability would be to measure frequency and amplitude of body sway in three dimension (3D) space while feet remain in a fixed position. This task can be performed in both a double or single leg stance to test for bilateral symmetry relating to balance. Another modification of the test would be to perform each test with eyes both open and closed to help determine the contribution of the visual component to overall balance ability. Tracking body sway while creating the illusion of motion through proper visual cueing on a display means would be another test to help determine the reliance on specific sensory components of balance. Delivering repetition of protocols with increasing difficult oscillation thresholds with biofeedback of successes and failures of such predetermined goals is one way to train to improve balance.

The transponder can deliver aural, visual, and tactile stimuli to queue the individual to the degree of frequency and amplitude of body oscillations. The aural and tactile components provide the only means of feedback when the testing and training are performed with eyes closed or the visual field is compromised. Examples include, but are not limited to, (1) an audio signal increasing and decreasing in volume proportional to the amplitude of body sway, (2) a vibration action proportional to frequency of body oscillations, and (3) a light source illuminated when both frequency and amplitude goals are achieved. Multiple transponders can be used to evaluate and reinforce proper balance posture by communicating position information of certain body segments in relationship to others. An example would be the comparison of position of the head with respect to the hips while generating a vibration action if an excessive forward lean of the head as compared to the hips is recognized.

Another test for balance would be to test ones Limits of Stability (LOS). This test refers to ones ability to effectively operate within their sway envelope. The sway envelope or LOS is defined as the maximal angle a person's body can achieve from vertical without losing balance. An individual with healthy balance is capable of leaning (swaying) within a known sway envelope and recover back to a centered position without the need for a secondary maneuver such as a step, excessive bend at the torso or arm swinging. LOS for bilateral stance in normal adults is 8 degrees anterior, 4 degrees posterior and 8 degrees laterally in both directions.

The present invention described can be used as a testing and training device for balance control during movement or perturbations within a desired sway envelope. Through proper visual queuing represented on the display means that defines a normal sway envelope, the amount of body displacement can be measured from vertical stance.

The transponder can deliver aural, visual, and tactile stimuli to queue the individual as to when he or she has achieved the desired range of their sway envelope, then assess the individual's ability to return back to a vertical stance. Examples include, but are not limited to, (1) a vibration action when the user varies (meanders) from the desired movement path, (2) an array of lights change intensity and pattern as the individual successfully approaches the intended target, (3) an audio signal is generated when the individual has maintained a stable position with respect to proper visual queuing represented on the display means for a selected period of time. Multiple transponders can be used to evaluate and reinforce proper balance posture by communicating position information of certain body segments in relationship to others. An example would be the comparison of position of the head with respect to the hips while generating a vibration action if an excessive forward lean of the head as compared to the hips is recognized.

Dynamic balance can be evaluated while having the individual perform coordinated movements which specifically challenge the various components of balance in a dynamic nature. Such movements include, but are not limited to jumping, hopping, and walking. These movements can be performed with eyes both open and closed, during interaction with static or dynamic visual queuing on the display means. The ability to perform these dynamic balance tasks with comparisons to others of similar sex, age or disability can be assessed. Example measurements may include, but are not limited to, (1) amount of body sway in three dimension (3D) space, (2) time to complete specific task, and (3) effects of fatigue on balance ability.

Balance training in both static and dynamic conditions can be easily achieved by providing specific visual queuing on the display means, which challenge the individual to perform repetitive and progressively more difficult balance drills. Performance reports can be generated to establish a baseline, isolate specific strengths and weaknesses within the specific sensory and motor control aspects of balance, and document progression and improvements.

The transponder can deliver aural, visual, and tactile stimuli to queue the individual as to when he or she has achieved the desired balance task. By example, a vibration action is produced proportional to the frequency of a body segment oscillation after the user lands from a hop test and attempts to stabilize and maintain proper postural balance. When the individual finally stabilizes and achieves correct postural balance, an audio signal indicates the task has successfully completed. Multiple transponders can be used to evaluate and reinforce proper balance posture by communicating position information of certain body segments in relationship to others. An example would be the comparison of position of the head with respect to the hips while generating a vibration action if an excessive forward lean of the head as compared to the hips is recognized.

Range of Motion (ROM)

The present invention described can be used as a testing and training device to determine the range of motion within a joint. Range of Motion is the normal distance and direction through which a joint can move. Limited ROM is a relative term indicating that a specific joint or body part cannot move through its normal and full ROM. Motion may be limited by a mechanical problem within the joint that prevents it from moving beyond a certain point, by swelling of tissue around the joint, by spasticity of the muscles, or by pain. Diseases that prevent a joint from fully extending, over time may produce contracture deformities, causing permanent inability to extend the joint beyond a certain fixed position.

The present invention described can be used to test the starting point and end point which an individual is capable of moving a body part, typically a limb and associated joint(s). Comparisons to age and sex based normative data can be made. Proper visual queuing can be represented on the display means to instruct and motivate the individual through the proper testing procedure.

The present invention described can be used as a testing and training device for individuals involved in physical rehabilitation or general fitness to improve ROM. Proper visual queuing can be represented on a display means to motivate individuals to extend their range of motion beyond their current capabilities.

The transponder can deliver aural, visual, and tactile feedback that alerts the individual to successes or failures in proper execution of each repetition. An example of tactile feedback would be the transponders are vibrated if the individual's movement trajectory varied from the intended two dimensional (2D) reference movement trajectory by deviation from the planar path into the uninvolved spatial dimension. An array of light sources could increase illumination in intensity and repetition as the ROM goal was approached and an audio tone could signal the individual they have achieved the desired pause time at the proper ROM.

Multiple transponders can be deployed to determine the contribution of each joint or anatomical structure where more then one joint is involved in the ROM movement (example; shoulder and scapular in overhead reaching). The vector sum of each transponder movement in a specific axis can be added together to determine the total ROM. The ROM of one joint in a two joint motion can be subtracted from the total ROM to determine the contribution of a single joint in a two joint movement.

Human Performance Testing and Training

There are many devices that test the strength and speed of isolated joint movements, for example, the leg extension and bicep curl. This information has value in testing both healthy individuals, athletes and individuals whose strength and speed capabilities may be compromised by injury, disease, poor conditioning or simply age. Recently in the field of human performance, it has been recognized that the analysis of the mobility of the isolated joint, although providing some value, does not offer enough information to determine how the body will perform during functional movements. Functional movements are defined as movements equal to those encountered on the athletic field, in the work environment or while performing activities of daily living. Functional movements involve the movement and coordination of multiple joints and muscle groups acting together to perform a more complex task then a single, isolated joint movement.

The present invention described can be used as a testing and training device for functional movement improvement. By tracking various registration points on the body with respect to each other or to an off-body registration point, performance measurements of functional movements can be assessed, such as jumping, cutting, turning, bounding, hopping, shuttling, etc.

The present invention described can be used as a testing and training device for individuals involved in physical rehabilitation, general fitness or sports performance enhancement to improve their functional movement abilities. Proper visual queuing can be represented on the display means to instruct and motivate individuals to perform specific functional movements.

The transponder can deliver aural, visual, and tactile feedback of proper movement execution. Examples include, but are not limited to, (1) an audio signal alerting the user that the desired performance stance is incorrect, (2) the light sources illuminate when the desired speed is achieved in a first step quickness drill, (3) a vibration action to indicate the limits of tracking range, (4) a vibration action proportional to the magnitude of a biophysical measurement during the interaction with visual queues represented on the display means, (5) a vibration action when the body or limb position does not correlate well to the desired body or limb position of the visual queuing represented on the display means, (6) an audio signal indicating start, stop and pause periods or other controlling events, (7) an audio signal indicating proper body alignment or posture has been compromised, and (8) an audio signal indicating the relationship of desired target heart rate to a desired threshold.

Hardware Description

Figure 5:
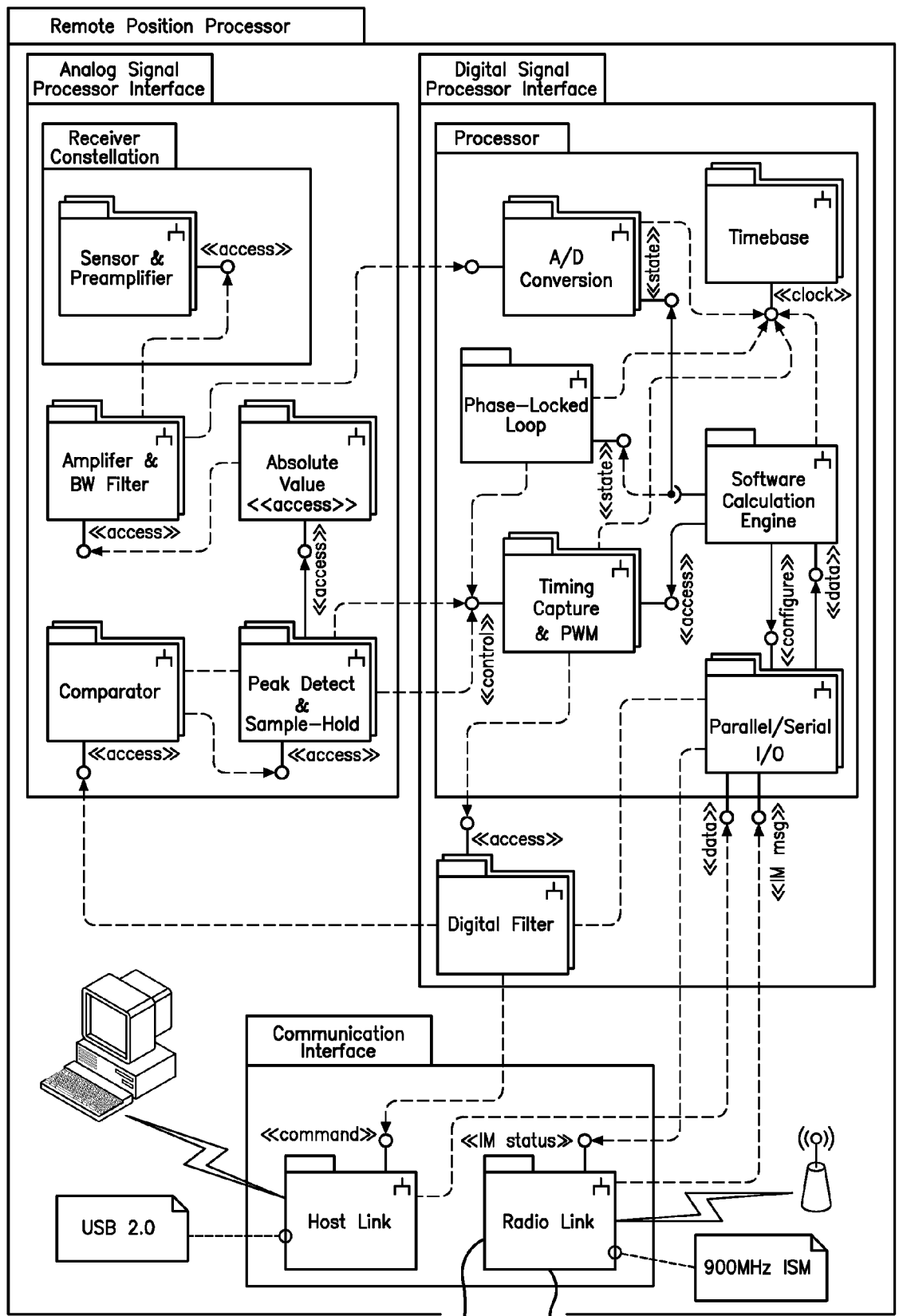
FIG. 5 illustrates a block diagram of the remote processing system of the present invention.

In the preferred embodiment, the processor unit is comprised principally of a constellation of five (5) ultrasonic transducers and signal processing circuitry, thereof, and a signal processor that interfaces to this receiver group, performs the pose calculations, and interfaces to the transponders and host computer databases. The following interface descriptions for the processor unit are based upon the dependency flow represented by FIG. 5.

The sensors 14 preferably used for the receiver constellation unit are cylindrically-shaped ultrasonic transducers, for example, the model US40KR-01 40 kHz PVDF ultrasonic receivers manufactured by Measurement Specialties Inc., which provide adequate acoustic pressure sensitivity and exhibit 360 degree omnidirectional broad beam response along the horizontal plane. The omnidirectional characteristic, albeit in one plane only, is very desirable to minimize line-of-sight occlusion. Because of its low resonance Q value, the rising and decay times are much faster than conventional ceramic transmitters. This reduces its power requirements since less burst drive duration is needed to achieve sufficient triggering thresholds at the receiver. This transducer type is also utilized similarly in the transponders to provide the potential for the most optimal acoustic coupling.

The receiver constellation unit is preferably mounted on a fixed support base, and has a pivoting and/or swiveling mechanical linkage which provides an adjustable mechanism for configuration of the receiver constellation unit's inertial frame of reference relative to the tracking field. In the preferred embodiment, it is strategically positioned and oriented in proximity to the tracking field in order (1) to minimize line-of-sight degradation with respect to the expected transponder orientation, (2) to optimize registration resolution with respect to field volume size, and (3) to satisfy the mathematical restrictions of performing trilateration calculations based upon the solution of simultaneous linear equations. It should be noted that the trilateration matrices may be solved if the matrices have a rank of five, and are non-singular, i.e., the matrix determinant is non-zero. In the preferred embodiment, the geometric parameters and their coordinate location of the receiver constellation must insure linear independence of the columns of the matrices and to avoid the matrices from becoming singular.

Figure 6A:
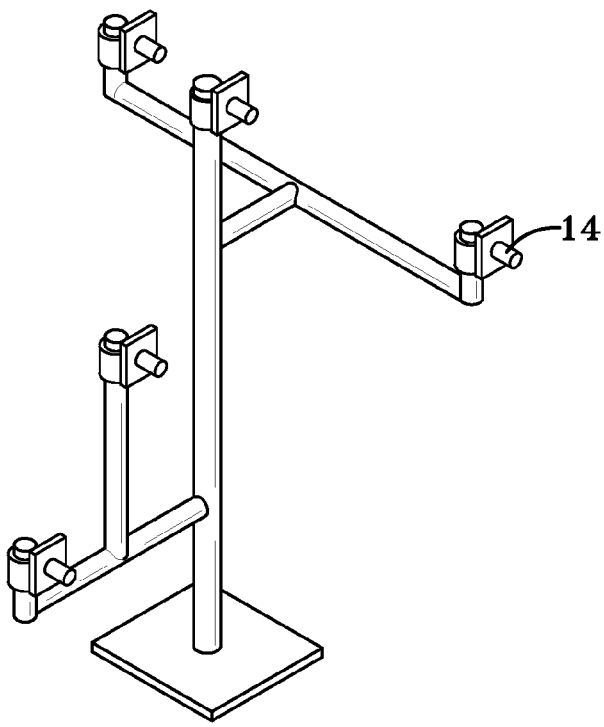
FIGS. 6A-6C illustrate example receiver configurations of the present invention.
Figure 6B:
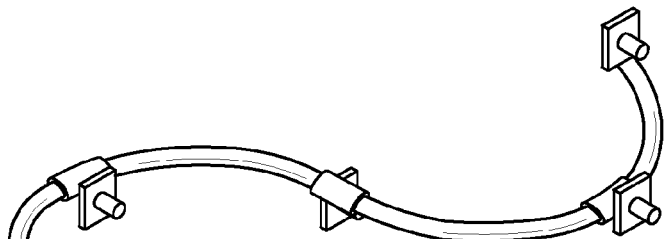
Figure 6C:
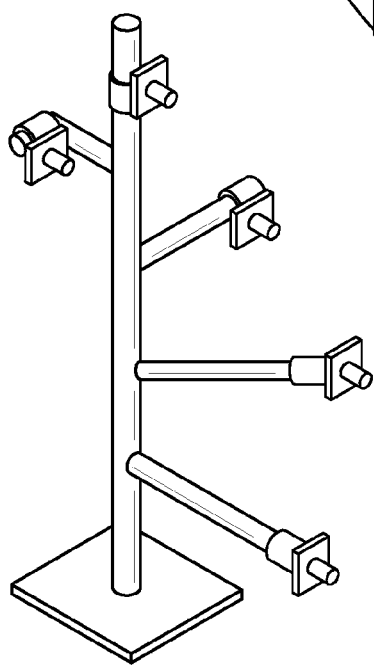
Figure 7:
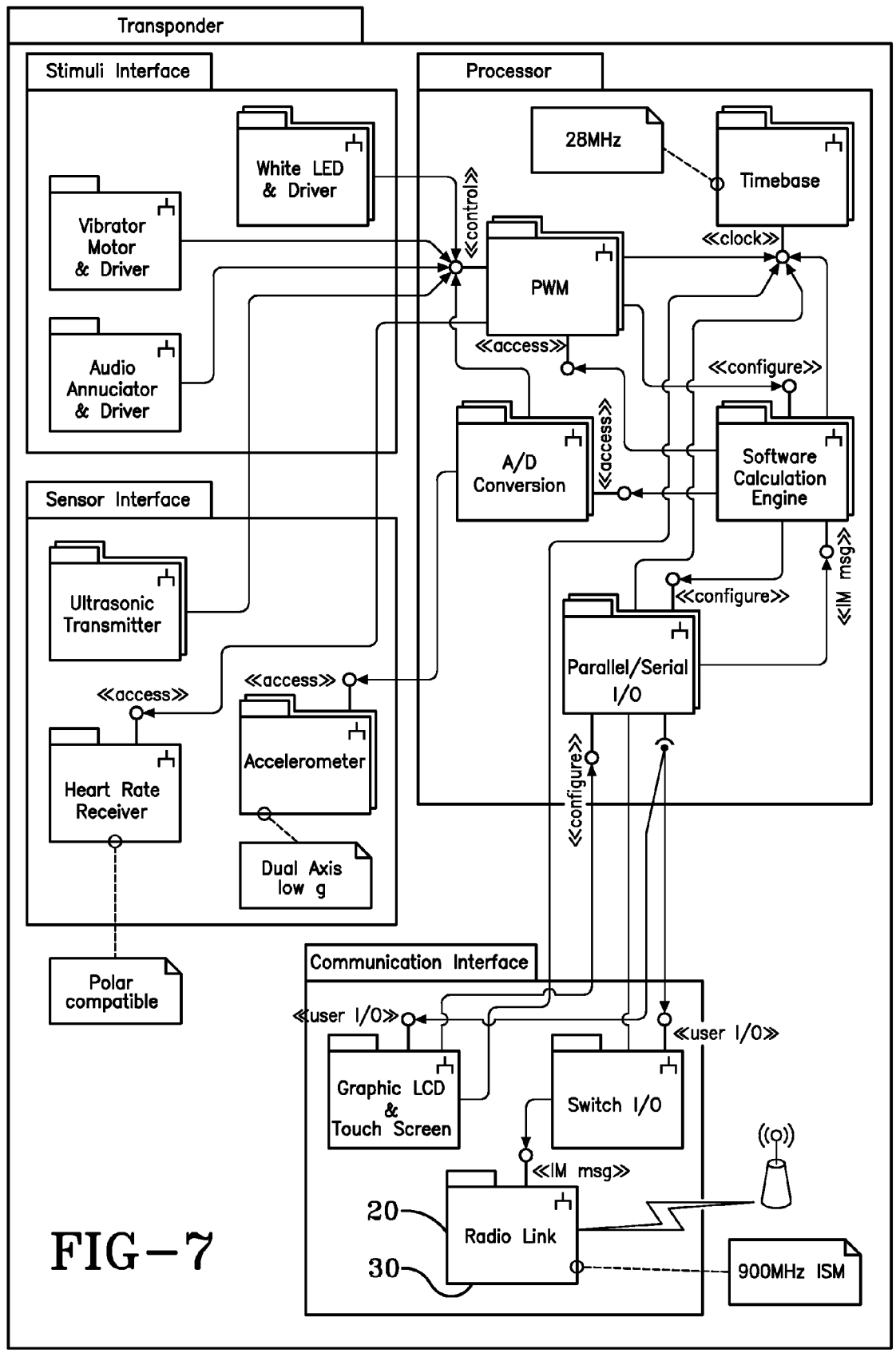
FIG. 7 illustrates a block diagram of the components of one embodiment of the transponder of the present invention.

One example of geometrical permutation of the receiver constellation unit that satisfies these rules is shown in FIG. 6A. It occupies a volume of approximately 8 cu. ft. and essentially fixes the transducers in a way that defines two primary orthogonal, bisecting planes defined by three non-collinear points each. Another preferred implementation that occupies nearly the same volume is shown in FIG. 6B and is characterized by its S-shaped curve and tilted with respect to the horizontal plane. Another preferred implementation that occupies nearly the same volume is shown in FIG. 6C and is characterized by its helical or logarithmic spiral shape oriented perpendicular to the horizontal plane. Further, as indicated in the preceding figures, the transducers vertical axes are oriented 90° with respect to the typical vertical axis orientation of the transponder's transmitter to improve acoustic coupling in the vertical plane, a consideration for overhead, upper extremity tracking. Although this causes some reduction in the lateral registration bounds, the compromise provides a more symmetric field about the middle or primary location of tracking interest.

In the preferred embodiment, the overall size of the receiver constellation unit is predicated on a phenomenon referred to as Geometric Dilution of Precision (GDOP). The solution of a unique three-dimensional location based upon trilateration requires the precise resolution of the common intersection of multiple spheres circumscribed by the distance between each transmitter and receiver transducer. Each sphere has an inexact radius due to system noise and measurement resolution. Therefore, the intersection becomes a volume instead of a point and the size of the volume is dependent upon the radii of the intersecting spheres as well as the distance between the spheres' centers. As the radii get larger with respect to the distance between the centers, i.e., the transmitter is farther down range, the spheres begin to appear more and more tangential to one another and the intersection volume increases, although not necessarily symmetrical in all dimensions. Therefore, to minimize position uncertainty, the receiver transducers should be separated from each other as much as practical proportions allow with respect to the confines of the tracking field volume as the above said geometric examples provide.

This receiver constellation unit can be repositioned with respect to the tracking field by a simple mechanical adjustment as shown in the preceding figures. The mechanical adjustment raises and lowers and changes the length and pivot axis of the cantilever arm which is fixed to a ground base support.

Because the receiver constellation unit operates a distance from the processor unit, each receiver preferably has an associated pre-amplifier circuit to convert the high-input impedance piezoelectric signal into a low-level voltage proportional to the acoustic signal energy impinging the transducers sufficient in order to accurately transmit the signals to the processor unit. In one embodiment, a high-input impedance AC amplifier design with 30 dB gain can be utilized. The preferred operational amplifier is the OPA373 manufactured by Texas Instruments. It was chosen for its low 1 pA input bias current, high 6 MHz GBW, and low-voltage single supply operation. The amplifier is configured as a non-inverting type with the high-pass cutoff frequency set at 1 kHz. The overall circuitry is preferably enclosed in a metal shield to minimize electromagnetic noise coupling into the highly sensitive amplifier inputs. In addition, a local, regulated power supply is included to allow for a wide range of input voltage supply and provide sufficient power supply rejection to compensate for the noise susceptibility of remote power distribution. All the pre-amplifier circuits' power and signal connections preferably originate from the processor unit.

The processor unit subsystem preferably consists of an analog signal processing interface that provides (1) additional voltage amplification and filtering of base band signal from the preamplifiers, (2) absqlute value function, (3) peak detection function, and (4) analog-to-digital comparator function to provide support for an adaptive threshold means. The adaptive threshold technique provides robust triggering of the most proximal ultrasonic source at a precise temporal point along the traversing sinusoidal waveform of the electrical signal. Essentially, a new threshold signal is recalculated each analysis period based upon a small percentage reduction of the last peak waveform detected. Therefore, the tracking range is not necessarily restricted due to an arbitrarily high threshold setting and the noise immunity is improved as the threshold tracks the waveform envelope and not transient disturbances. An alternative automatic gain control strategy for the amplification function is unnecessary since the trigger threshold will adjust to the signal level instead. In the preferred embodiment, the threshold faithfully tracks the peak to minimize integer period phase errors, so the amplifier's gain is set to prevent signal saturation from occurring when the receiver constellthion unit and transponders are in closest proximity during normal use.

In one embodiment, an amplifier and BW (band width) filter circuit receives the output from the sensor and preamplifier circuit and provides additional amplification and low-pass filtering to condition it for reliable threshold triggering and input to other analog signal processing circuitry. A dual amplifier configuration may be used to provide an additional gain of 40 dB, AC coupling to remove DC offsets of the preamplifier outputs and long cable losses, and low-pass filter to reject noise beyond the interest signal's bandwidth. The first stage amplifier may be configured as a non-inverting type with a gain of 20 dB. The low-impedance DC input signal is effectively blocked by the coupling capacitor in series at its non-inverting input with a high-pass frequency cutoff set at 20 kHz. This gain stage feeds a second amplifier configured as low-pass, $2^{nd}$ order Butterworth MFB filter. This filter type provides smooth pass band response and reduced sensitivity to component tolerances. The second stage low-pass frequency cutoff is set at 80 kHz with a pass band gain of 20 dB.

An absolute value circuit receives the output of the amplifier and BW filter circuit and converts the bipolar signal into a unipolar form for magnitude detection. A dual amplifier configuration may be used to provide highly accurate full wave rectification of the millivolt-level signal. The first stage amplifier feedback switches to control the distribution of input current between the two signal paths dependent upon the input signal polarity. For a positive input voltage the input current will be positive which forward biases D1 and reverse biases D2. This configures the $1^{st}$ stage as an inverter driving the inverting input resistor of the $2^{nd}$ stage, which is also configured as an inverter because its non-inverting input is held at virtual ground due to the non-conducting path of D2. This effectively creates a combined circuit of two cascaded inverters for an overall gain of +1. For a negative input signal its input current is negative which forward biases D2 and reverse biases D1. This configures the $1^{st}$ stage as an inverter driving the non-inverting input of the $2^{nd}$ stage which changes the sign of the circuit gain. In this mode, the input current is shared between two paths to the input of the $2^{nd}$ stage, where $-\frac{2}{3}$ of the input current flows around the $1^{st}$ feedback stage and $-\frac{1}{3}$ flows in the opposite path around the $2^{nd}$ stage feedback path for a net gain of $-1$.

In the preferred embodiment, a peak detect and sample-hold circuit receives the output of the absolute value circuit and registers a peak value that is required to set a magnitude threshold precisely at some percentage of full-scale of the peak. A dual amplifier configuration may be used to provide the highest ratio of high output slew rate to low droop. The first stage is typically in negative saturation until the input voltage rises and exceeds the peak previously stored on the sample capacitor at the inverting input. Now the amplifier acts as a unity gain buffer and the input voltage charges the sample capacitor which faithfully tracks the rising voltage. Once the input voltage diminishes in magnitude, the first blocking diode reverse biases and the sample capacitor holds an accurate replica of the highest voltage attained with minimal droop because of the low input bias current of the amplifier and elimination of leakage altogether in the second blocking diode by bootstrapping its cathode at the same potential provided by the low-impedance buffer of the second output stage. An electronic switch and bleed resistor allow the voltage across the sample capacitor to be reset by the processor during power up and after the triggering event is recorded so the adaptive threshold value can be refreshed each cycle. A $1^{st}$ order Butterworth filter may be used at the input to smooth false in-band transients that could disrupt the peak accuracy detection.

In the preferred embodiment, a comparator circuit receives the output from the peak detect and sample-hold circuit to convert the analog signal to digital form for high-speed triggering operation of the processor. The preferred device is the MAX941 which is manufactured by Maxim. A percentage of the peak threshold is used to set the inverting input. When the non-inverting voltage exceeds the inverting voltage, the comparator's output will trip and produce a high-true logic pulse that triggers the processor. A latch control input allows the processor to disable the comparator action to prevent unnecessary triggering during the reverberation phase and to prevent potentially disruptive noisy output chattering near threshold crossover beyond its hysteretic immunity. The percentage of threshold level is predetermined through the scaling resistors to be set low enough to trigger on the rising edge of the signal's first crest at the furthest range of transponder operation, but high enough above the intrinsic system noise level and external noise caused by reverberation and other ultrasonic sources. Once the first crest is registered, subsequent crests may be triggered at their zero-crossing representing the most precise timing registration by momentarily disabling the sample-hold circuit. Because of the longer duration trigger receptivity window, early multiple reflections are mitigated by transducer placement at least 3.5 cm away from adjacent planar surfaces, so the reflected acoustic energy doesn't produce a canceling effect of the direct acoustic energy of the later crests. Once a sufficient number of crests have been registered, then the triggering window is blanked for the remainder of the analysis period by latching the comparator's value.

In the preferred embodiment, a digital signal processing interface is connected to the analog signal processing interface to transform the analog trigger processing into digital position information.

The digital filter circuit receives output from the comparator circuit and preferably consists of a digital low-pass filter implemented in a complex programmable logic device (CPLD) that serves to precondition the comparator circuit's digital outputs. The preferred device is an AT1504ASVL CPLD which is manufactured by Atmel. Base band system noise or other glitches potentially occurring in the analog signal processor interface, but prior to the actual arrival of the ultrasonic signal, could cause a threshold disruption that registers a "runt" pulse as a false trigger condition. The "runt" pulse would be misinterpreted as the actual TOF trigger and cause serious error in the position calculation. An AND/NOR one-hot state machine design may be used to ignore level transitions that are not stable for at least ½ system clock frequency×8 states, so only transitions of 4 μS or greater are passed through. The system clock delays introduced by the digital filter's synchronous state machine affect all channels the same and are, therefore, effectively eliminated by the inherent dependency on relative measurement.

In the preferred embodiment, the processor and digital filter circuits receive the output from the analog processor and provide controlling signals therein. The preferred processor circuit is the MC9S08 GB60 which is manufactured by Motorola Inc. It is a low-cost, high-performance 8-bit microcontroller device that provides all the aforementioned hardware circuits integrated into one convenient device. The calculation circuit is abstracted from embedded 60 KB FLASH for program memory with in-circuit programmable capability and 4 KB RAM for data memory. The time base circuit is preferably comprised of an external, high-noise immunity, 4.0 MHz system clock, which multiplies this by the internal frequency-locked loop for a bus clock of 40.0 MHz and single instruction execution time of 25 ηS. This clock also provides all the capture and control timing functionality for the other specified circuits. Multiple parallel I/O ports and dedicated asynchronous serial communication signals provide for the digital control of the analog signal processing and communication interfaces, respectively.

The timing capture-control circuit receives the output from the digital filter circuit representing the arrival of the TOF triggers to determine the relative TOF propagation of the ultrasonic acoustic wave as it passes through the receiver constellation unit. More specifically, it is comprised of a five channel 16-bit timer input capture module with programmable interrupt control that provides edge detection and 50 ηs timing precision to automatically register the TOF triggers timestamps asynchronously without using inefficient and less accurate software polling means.

The phase-locked loop circuit receives the output from the timing capture-control circuit and is preferably comprised of a three channel, 16-bit timer compare module is implemented as an all-digital phase locked loop (ADPLL), which synchronizes the capture window and blanking functions with respect to the reference input channel. It is comprised primarily of a free-running 16-bit timer configured to periodically interrupt the processor dependent upon a precise convergence of its period and phase to the reference trigger source, by means of an over/under count matching and correction technique.

The ND conversion circuit receives the output from the amplifier and BW filter circuit and consists of an eight channel 10-bit analog-to-digital converter used to monitor channel offsets and magnitudes for range and polarity errors and correction. This information is utilized by the calculation circuit as input to the TOF software correction algorithm to determine the slope of the waveform crest.

In the preferred embodiment, the serial communication circuit is comprised of two asynchronous serial communication interfaces that are connected between the calculation circuit and host link and radio link circuits of the communication interface. The host link provides a 115K bit per second (baud) bi-directional communication link to an auxiliary host computer system through a Serial-to-Universal Serial Bus bridge. The preferred device is the CP2101 which is manufactured by Silicon Laboratories. It supports the conversion of a fully asynchronous serial data bus protocol, with buffering and handshaking support, to an integrated Universal Serial Bus (USB) Function Controller and Transceiver and internal clock providing USB 2.0 full-spded compliancy. An integrated 512 bit EEPROM stores the required USB device descriptors, including the Vendor ID, Product ID, Serial Number, Power Descriptor, Release Number and Product Description Strings. A host computer may enumerate and access this device utilizing the manufacturer's virtual COM port device drivers using a USB channel.

In the preferred embodiment, the radio link circuit is comprised of a wireless bi-directional communication interface to preferably (1) broadcast a synchronization signal to control the transponders interoperability, (2) to receive other transponder sensor data, including, but not limited to, accelerometer, heart rate, battery, user I/O status, (3) to provide control messages for the transponders' sensory interfaces, and (4) to provide means to configure transponders' local databases. The preferred wireless communication link is based upon the AT86RF211, a highly integrated, low-power FSK transceiver optimized for license-free ISM band operations from 400 MHz to 950 MHz and manufactured by Atmel. It supports data rates up to 64 kbps with data clock recovery and no Manchester Encoding required. The device has a three wire microprocessor interface that allows access of read/write registers to setup the frequency selection, transmission mode, power output, etc. or get information about parameters such as battery, PLL lock state, etc. In normal mode, any data entering its input channel is immediately radiated or any desired signal collected by the aerial is demodulated and transferred to the microprocessor as reshaped register bit information. In wake-up mode, the device periodically scans for an expected message sequence and broadcasts an interrupt if a correct message is detected.

In the preferred embodiment, at least three (3) consecutive TOF timestamps are registered for each receiver during the acquisition phase. Preferably, the transponder's transducer emits a multi-cycle ultrasonic acoustic burst of at least ten cycles in duration so that sufficient energization of the receiver transducer is realized and at least three crests of the waveform can be properly registered. At low signal levels when ultrasonic acoustic coupling is poor, this requirement may fail and an invalid tracking status is asserted. Preferably, the reference receiver transducer of the receiver constellation unit is positioned in closest proximity to the acoustic signal source so that it is the first transducer to be affected by the initial wave front. This reference receiver provides the overall system timing and state machine control for the phase-locked loop circuit, so that the processing, calculation, and communication tasks are executed in a deterministic and efficient fashion.

It should be appreciated that a high-resolution ultrasonic acoustic tracking system that depends upon threshold detection means has an inherent uncertain trigger dilemma. This uncertainty arises because of the multi-cycle nature of the transmitted signal's waveform and the associated difficulty detecting the exact temporal location for consecutive analysis periods when the signal's magnitude may vary greatly depending upon the efficiency of the acoustic coupling, the distance between transmitter and receiver, and signal-to-noise ratio of the signal processing techniques. If a threshold is set near one of the minor crests of the waveform during the last analysis period, then it is conceivable a slight reduction of magnitude of the waveform during the next analysis period may fall slightly below the set threshold and actually not be triggered until the next larger excursion of the waveform occurs. This would create a TOF error proportional to the period of the acoustic waveform or its intra-pulse interval and have a detrimental affect on the measurement accuracy. This analog processing described above establishes trigger thresholds that allow no more than a single intra-pulse interval of uncertainty, but that is still inadequate for high-resolution measurements. Although a technique is known that controls the largest peak profile of the transmitter acoustic signal and claims to provide an absolute trigger condition, this procedure is difficult to reliably tune and control among different transducer types.

In the preferred embodiment of the invention, no modulation of the acoustic signal is required. Rather, the adaptive threshold method is augmented with a TOF software correction algorithm that unambiguously determines the correct TOF based upon a means to detect the same carrier wave cycle of ultrasonic energy every period. The software correction algorithm requires multiple, consecutive TOF acquisitions as input for the digital over-sampling and averaging algorithm, the calculation of a higher-order numerical differentiation of the past and current TOF information as input for the predictive algorithm of higher-order Taylor series based derivatives used for the relative TOF correction, and a measurement of the intra-pulse time intervals of consecutive TOF acquisitions as input for the absolute TOF correction scheme that minimizes the range error based upon selective biasing of the TOFs.

The calculation circuit preferably processes multiple, consecutive TOF acquisitions to effectively improve the timing resolution that proportionally affects position accuracy and precision. The digital filter discussed above introduces quantization errors because of its discrete operation. And minor fluctuations in the acoustical coupling produces timing jitter or uncertainty in the triggered zero-crossings of the acoustic sinusoidal. A Gaussian average or mean value of multiple TOF is a simple and effective filter strategy. Due to the possibility of poor acoustic coupling or misalignment, and distant transponder location from the processor unit, the number of detectable triggered zero-crossings may vary for a fixed duration of multi-cycle ultrasonic acoustic burst. The averaging algorithm automatically adjusts to this condition by only including TOFs whose delta changes fall within the expected range of the nominal intra-pulse interval defined by the transmission properties of the acoustic source. The nominal intra-pulse interval is determined and utilized by the following compensation schemes.

The calculation circuit preferably processes a relative TOF correction algorithm based upon a predictive tuned algorithm that requires higher-order numerical differentiation calculation of the past and current TOFs. This compensates the TOFs that may have registered one intra-pulse interval earlier or later than the nominally expected time due to the trigger dilemma described above. By formulating these derivatives into a truncated $2^{nd}$ order Taylor series expansion and weighting the terms contribution, an estimate of expected TOF is calculated and compared to the actual TOF through an iterative error minimization calculation. A minimized error that results in a delta time change indicative of a discrete intra-pulse interval increase or decrease due to an early or late TOF, respectively, produces a characteristic value that directs the algorithm to compensate the actual TOF by the intra-pulse interval and restore it to its correct value. In the preferred embodiment, this relative compensation algorithm works most effectively when, (1) the maximally expected inter-period TOF change is less than the discrete intra-pulse interval, (2) the TOF inter-period processing is contiguous, (3) the TOF increase or decrease is no more than a single intra-pulse interval, and (4) the Taylor series terms are suitably weighted in the prediction algorithm.

The calculation circuit preferably processes an absolute TOF correction algorithm at least once initially, when the phase-locked loop is stable, but may be performed every analysis period depending on computational resources, that determines the initial set of TOF values for the relative correction algorithm. The initial condition that precedes the start of the relative compensation algorithm may be due to the resumption of a stable, locked tracking state after recovery from a fault condition and, therefore, requires computation of a set of reference TOFs producing minimum range error as a starting basis. The algorithm utilizes a wireless synchronization means to determine a reference TOF calculation between the transponder and reference sensor of the receiver constellation. By computing the reference range distance by the product of the reference TOF and speed of sound in air, this reference range may be compared to the range calculated from the matrices solutions described below. By iteratively and sequential increasing and decreasing the TOFs by a single intra-pulse time interval and applying the input to matrices formulations described below, all possible combinations of compensation are permutated and tested, which produces a unique set of TOFs that minimize the error between the calculated range distance with respect to the reference range distance. This unique set of initial TOFs serves as the starting basis for the relative compensation algorithm. In the preferred embodiment, this absolute compensation algorithm works most effectively when (1) the wireless synchronization means is tightly coupled to the excitation of the acoustic source, (2) the synchronizing signal's arrival is timed by the same mechanism that times the arrival of the reference transducer's acoustic signal, and (3) the coordinate locations of the sensors of the receiver constellation are established to a high degree of accuracy.

The calculation circuit preferably employs two software methods of trilateration calculation to estimate transponder position, wherein the particular method used depends upon the availability of a synchronizing signal and the accuracy desired. The first method is based on a relative TOF calculation and the speed of sound is treated as a constant estimated at ambient indoor room temperature. The second method requires calculation of an additional TOF timestamp between the transponder and reference receiver, but calculates the speed of sound as an unknown every analysis period, and thus improves measurement accuracy. The first method eliminates the global system timing variances and delays due to the multiplicity of signal conditioning circuitry and eliminates the need for a controlling signal means synchronized at the generation of the transmission of the ultrasonic acoustic wave. The second method also employs relative TOF calculation but requires an additional synchronization signal from the processor unit to determine the absolute TOF between transponder and reference receiver. Since the absolute TOF is based upon a single channel only, its timing latencies can be readily accounted for and easily corrected. This method computes the speed of sound every analysis period, provided the synchronization signal is detected, without need for additional hardware temperature processing or requiring more then five (5) receivers, and automatically accounts for the system's main accuracy limitation of speed of sound in air as defined by Eq. 1.1, if uncorrected, yields a 1.6 mm/m ranging error for every 1° C. temperature shift. If the synchronization signal is not detected and, therefore, the second method is not resolvable, the last calculated speed of sound can be utilized within the first method's calculation to minimize error.

$$c \approx 34.6 \text{ m/s} + 0.5813 \text{ m/s}(T_c - 25° \text{ C.}) \tag{1.1}$$

The TOF timestamps and speed of sound values are input into linear independent algebraic equations in a matrix formulation to solve for the unknown transponder(s) position, in a form as shown in Eq. 2.1, $$A \cdot X = B \tag{2.1}$$

$$A = \begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix}$$

$$X = \begin{bmatrix} x_1 \\ x_2 \\ x_3 \\ x_4 \end{bmatrix}$$

$$B = \begin{bmatrix} b_1 \\ b_2 \\ b_3 \\ b_4 \end{bmatrix}$$

To solve for the unknowns X, Eq. 2.1 is rearranged as shown in Eq. 3.1, whereas the inverse of A requires computation of the cofactor matrix $A^c$ for the adjoint and determinant calculations for Eq. 3.2 and Eq. 3.3, respectively, $$X = A^{-1} \cdot B = \frac{(A^c)^T}{|A|} \cdot B \tag{3.1}$$

$$(A^c)^T = \begin{bmatrix} A_{11} & A_{21} & A_{31} & A_{41} \\ A_{12} & A_{22} & A_{32} & A_{42} \\ A_{13} & A_{23} & A_{33} & A_{43} \\ A_{14} & A_{24} & A_{34} & A_{44} \end{bmatrix} \quad (3.2)$$

$$|A| = a_{11} \cdot A_{11} + a_{21} \cdot A_{21} + a_{31} \cdot A_{31} + a_{41} \cdot A_{41} \quad (3.3)$$

To setup the coefficient matrix A, the utilization of five (5) receivers produces the following set of relative TOF equations defined by Eqs. 4.1-4, $$\Delta T_{12} = T_2 - T_1 \quad (4.1)$$

$$\Delta T_{13} = T_3 - T_1 \quad (4.2)$$

$$\Delta T_{14} = T_4 - T_1 \quad (4.3)$$

$$\Delta T_{15} = T_5 - T_1 \quad (4.4)$$

The receiver locations are fixed within the system's inertial reference frame, while the transponder(s) are mobile with respect to the same reference frame and are defined as follows, $S(x_i, y_i, z_i)$ for $5 \geq i \geq 1 \Rightarrow$ fixed receiver locations)

$S(x_0, y_0, z_0) \equiv S(u, v, w) \Rightarrow$ unknown transponder location

Since each receiver is fixed at a distance $D_i$ from the transponder as determined by the receiver constellation geometry and because the acoustic waves propagate spherically, by using Pythagorean's theorem the following set of range equations are defined in Eqs. 5.1-5, $$(x_1 - u)^2 + (y_1 - v)^2 + (z_1 - w)^2 = D_1^2 \quad (5.1)$$

$$(x_2 - u)^2 + (y_2 - v)^2 + (z_2 - w)^2 = D_2^2 \quad (5.2)$$

$$(x_3 - u)^2 + (y_3 - v)^2 + (z_3 - w)^2 = D_3^2 \quad (5.3)$$

$$(x_4 - u)^2 + (y_4 - v)^2 + (z_4 - w)^2 = D_4^2 \quad (5.4)$$

$$(x_5 - u)^2 + (y_5 - v)^2 + (z_5 - w)^2 = D_5^2 \quad (5.5)$$

Equivocally, the four (4) non-reference receivers are preferably located at an incremental distance relative to the reference receiver, so by substitution of the incremental distance defined by Eq. 6.1, the following set of relativistic range equations are defined by Eqs. 6.2-5, $$D_i = D_1 + c\Delta T_{1i} \text{ for } 5 \geq i \geq 2 \quad (6.1)$$

$$(x_2 - u)^2 + (y_2 - v)^2 + (z_2 - w)^2 = (D_1 c\Delta T_{12})^2 \quad (6.2)$$

$$(x_3 - u)^2 + (y_3 - v)^2 + (z_3 - w)^2 = (D_1 c\Delta T_{13})^2 \quad (6.3)$$

$$(x_4 - u)^2 + (y_4 - v)^2 + (z_4 - w)^2 = (D_1 c\Delta T_{14})^2 \quad (6.4)$$

$$(x_5 - u)^2 + (y_5 - v)^2 + (z_5 - w)^2 = (D_1 c\Delta T_{15})^2 \quad (6.5)$$

By expanding and rearranging the terms of Eqs. 6.2-5, a set of four linear algebraic equations and four unknowns for the first method algorithm, depicted in the matrix form of Eq. 2.1, is defined by Eq. 7.1, $$2\begin{bmatrix} x_1 - x_2 & y_1 - y_2 & z_1 - z_2 & -c\Delta T_{12} \\ x_1 - x_3 & y_1 - y_3 & z_1 - z_3 & -c\Delta T_{13} \\ x_1 - x_4 & y_1 - y_4 & z_1 - z_4 & -c\Delta T_{14} \\ x_1 - x_5 & y_1 - y_5 & z_1 - z_5 & -c\Delta T_{15} \end{bmatrix} \begin{bmatrix} u \\ v \\ w \\ D_1 \end{bmatrix} = \quad (7.1)$$

$$\begin{bmatrix} (c\Delta T_{12})^2 + R_1^2 - R_2^2 \\ (c\Delta T_{13})^2 + R_1^2 - R_3^2 \\ (c\Delta T_{14})^2 + R_1^2 - R_4^2 \\ (c\Delta T_{15})^2 + R_1^2 - R_5^2 \end{bmatrix}$$

where $R_i^2 = x_i^2 + y_i^2 + z_i^2$ for $5 \geq i \geq 1$ \quad (7.2)

Alternatively, if the second method algorithm is used, the unknown range of the reference receiver $D_1$ can be substituted by Eq. 8.1, $D_1 = cT_{01}, \Delta T_{01} \Rightarrow$ time of flight (TOF) from $S(u,v,w)$ to $S(x_1, y_1, z_1)$ \quad (8.1)

And, by rearranging terms, it is depicted in the matrix form defined by Eq. 9.1, a.

$$2\begin{bmatrix} x_1 - x_2 & y_1 - y_2 & z_1 - z_2 & -(\Delta T_{01}\Delta T_{12} + 0.5\Delta T_{12}^2) \\ x_1 - x_3 & y_1 - y_3 & z_1 - z_3 & -(\Delta T_{01}\Delta T_{13} + 0.5\Delta T_{13}^2) \\ x_1 - x_4 & y_1 - y_4 & z_1 - z_4 & -(\Delta T_{01}\Delta T_{14} + 0.5\Delta T_{14}^2) \\ x_1 - x_5 & y_1 - y_5 & z_1 - z_5 & -(\Delta T_{01}\Delta T_{15} + 0.5\Delta T_{15}^2) \end{bmatrix} \begin{bmatrix} u \\ v \\ w \\ c^2 \end{bmatrix} = \quad (9.1)$$

$$\begin{bmatrix} R_1^2 - R_2^2 \\ R_1^2 - R_3^2 \\ R_1^2 - R_4^2 \\ R_1^2 - R_5^2 \end{bmatrix}$$

Although similar results may be obtained by application of more computational efficient processes such as pivotal condensation or Crout's decomposition, the application of Cramer's rule was used to evaluate the first-order determinant in Eq. 3.3 using second-order determinants from Laplace expansion. The final transponder(s) position equations are defined by Eqs. 10.1-8.

$$u = \frac{|A_2|}{|A|} \quad (10.1)$$

$$v = \frac{|A_2|}{|A|} \quad (10.2)$$

$$w = \frac{|A_3|}{|A|} \quad (10.3)$$

$$D_1 = \frac{|A_4|}{|A|} \text{ (1st method) or } c = \sqrt{\frac{|A_4|}{|A|}} \text{ (2nd method)} \quad (10.4)$$

$$|A_1| = b_1 \cdot A_{11} + b_2 \cdot A_{21} + b_3 \cdot A_{31} + b_4 \cdot A_{41} \quad (10.5)$$

$$|A_2| = b_1 \cdot A_{12} + b_2 \cdot A_{22} + b_3 \cdot A_{32} + b_4 \cdot A_{42} \quad (10.6)$$

$$|A_3| = b_1 \cdot A_{13} + b_2 \cdot A_{23} + b_3 \cdot A_{33} + b_4 \cdot A_{43} \quad (10.7)$$

$$|A_4| = b_1 \cdot A_{14} + b_2 \cdot A_{24} + b_3 \cdot A_{34} + b_4 \cdot A_{44} \quad (10.8)$$

If the first method is used, D, the range of the transponder to the reference receiver from Eq. 10.4 may be calculated as a redundant confirmation of the Eqs. 10.1-3 calculations, provided the frame of reference origin and location of the reference receiver are identical or their offsets accounted for. If the second method is used, C, the speed of sound in air, from Eq. 10.4 must be computed every analysis period if its value is anticipated to be used in the first method in the absence of a synchronization signal.

The orientation of the transponders can be derived from a similar utilization of the above algorithms for a transponder configured with a triad of ultrasonic transmitters. The transducers are preferably arranged in a triangular plane at the transponder of sufficient area for the desired angular resolution. The sequential excitation of each transducer and subsequent calculation of position by the aforementioned methods provides sufficient information to determine orientation by the inverse kinematic calculations of Eqs. 11.1-4, where the analysis is simplified by assuming the origin of rotations occurs about $T_1$ and $T_{123}$ represents the initial relative position matrix from this origin and $T'_{123}$ is the transformed or forward kinematic position matrix.

$$R_z(\theta)^{-1} T'_{123} = R_x(\theta) R_y(\theta) T_{123} \quad (11.1)$$

$$R_x(\theta) R_y(\theta) T_{123} \equiv \begin{bmatrix} 0 & x_2 \cos\theta_y + z_2 \sin\theta_y & x_3 \cos\theta_y \\ 0 & \sin\theta_x(x_2 \sin\theta_y - z_2 \cos\theta_y) & x_3 \sin\theta_x \sin\theta_y \\ 0 & -\cos\theta_x(x_2 \sin\theta_y - z_2 \cos\theta_y) & -x_3 \cos\theta_x \sin\theta_y \end{bmatrix} \quad (11.2)$$

$$R_z(\theta)^{-1} T'_{123} \equiv \quad (11.3)$$
$$\begin{bmatrix} x'_1 \cos\theta_z + y'_1 \sin\theta_z & x'_2 \cos\theta_z + y'_2 \sin\theta_z & x'_3 \cos\theta_z + y'_3 \sin\theta_z \\ -x'_1 \sin\theta_z + y'_1 \cos\theta_z & -x'_2 \sin\theta_z + y'_2 \cos\theta_z & -x'_3 \sin\theta_z + y'_3 \cos\theta_z \\ z'_1 & z'_2 & z'_3 \end{bmatrix}$$

$$\because x_1 = y_1 = z_1 = 0 \wedge y_2 = 0 \wedge y_3 = z_3 = 0 \text{ for initial orientation} \quad (11.4)$$

By examination of the matrices element equivalency of Eqs. 11.2-3 and manipulation of terms so that the angles may be found using the inverse tangent function, the following rotation Eqs. 12.1-3 are derived, $$\theta_x = a\tan\left(\frac{x'_2 \sin\theta_z - y'_2 \cos\theta_z}{z'_2}\right) \quad (12.1)$$

$$\theta_y = a\tan\left(\frac{-z'_3}{\cos\theta_x(x'_3 \cos\theta_z + y'_3 \sin\theta_z)}\right) \quad (12.2)$$

$$\theta_z = a\tan\left(\frac{y'_3 - \frac{x_3 \sin\theta_x \sin\theta_y}{\cos\theta_{z-1}}}{x'_3}\right) \quad (12.3)$$

$$\cos\theta_{z-1} \equiv \cos\theta_z \text{ from previous iteration} \quad (12.4)$$

$$\theta_z = a\tan\left(\frac{y'_3}{x'_3}\right) \text{ for 1st iteration} \quad (12.5)$$

These calculations are performed through iterative step processes which inherit angular approximations of the preceding steps until the final desired angular accuracy is achieved by assuming the conditions of Eqs. 12.4-5. Therefore the rotation $\theta_z$, roll, is first approximated by Eq. 12.5; then the rotation $\theta_x$, pitch, is approximated by Eq. 12.1; and then the final rotation $\theta_y$, yaw or turn, is approximated by Eq. 12.2. The next approximation of $\theta_z$ utilizes the previous value of $\theta_z$ in Eq. 12.3 and the similar steps are preferably repeated until the desired accuracy is achieved. The transcendental functions may be evaluated through a conventional look-up table or by a power series expansion.

Preferably, the overall analysis period duration is effectively trebled until the three (3) transducers' positions are calculated, which reduces the system's frequency response and imposes an increased latency effect. Typically, robust absolute orientation processing requires more stringent line-of-sight operation and is reserved for more sensitive, less dynamic, and reduced ROM movement trajectories, e.g., balance and sway. Therefore, the latency effect is less noticeable upon the real-time performance of the sensory interfaces.

In the preferred embodiment, the interactive hand-held transponders support a dual axis inertial sensor, which is operably configured to provide tilt (pitch and roll) orientation in its horizontal mounting plane. The inertial sensor is mounted in the intended operational horizontal plane with respect to the systems inertial frame of reference. Once the sensors signals has been converted to an acceleration value that varies between +/−1 g the tilt in degrees is calculated as shown in Eqs. 13.1-2, for pitch and roll, respectively.

$$\phi = a \sin(A_x/1 \text{ g}) \quad (13.1)$$

$$\phi = a \sin(A_y/1 \text{ g}) \quad (13.2)$$

This outside-in ultrasonic tracking implementation, where the transponders are mounted on the mobile object, produces inherent temporal delays due to the finite TOF registration and calculation delays after the transponder has already moved into a different position before the measurement is complete. This overall latency period is compensated and minimized through use of a Kalman filter data processing algorithm to estimate the pose of the transponder by optimally and recursively combining past history, new measurements, and a priori models and information. Generally speaking, the Kalman filter is a digital filter with time-varying gains that are optimally determined through a stochastic dynamical model of the motion. The overall goal is to minimize filter lag while providing sufficient smoothing of the motion data.

An adaptive, multi dynamic model is developed based upon the kinematic quality of the expected movement trajectory. The predictive kinematic model for the Kalman filter is depicted in matrix form utilizing a truncated $2^{nd}$ order Taylor series expansion as below in Eqs. 14.1-2, $$\begin{bmatrix} r \\ v \end{bmatrix}_{k+1} = \begin{bmatrix} 1 & \Delta t \\ 0 & 1 \end{bmatrix} \begin{bmatrix} r \\ v \end{bmatrix}_k + \begin{bmatrix} 0 \\ w \end{bmatrix} \quad (14.1)$$

$$\begin{bmatrix} r \\ v \\ a \end{bmatrix}_{k+1} = \begin{bmatrix} 1 & \Delta t & 0.5\Delta t^2 \\ 0 & 1 & \Delta t \\ 0 & 0 & 1 \end{bmatrix} \begin{bmatrix} r \\ v \\ a \end{bmatrix}_k + \begin{bmatrix} 0 \\ 0 \\ w \end{bmatrix} \quad (14.2)$$

The Kalman filter is now described for a single dimension, although it is utilized for prediction and smoothing for all position dimensions. The predictor stages consist of the calculation of the state and the error covariance projection equations. The state projector equation, Eq 15.1, utilizes a discrete time-sampled difference equation of r calculated from Eq. 15.2. In other words, the numerically derived velocity and acceleration components of motion are linearly combined with the previously a priori position to estimate the new position. The corrector stages consist of sequential computation of the gain, updated state estimate, and updated error covariance equations. The a posteriori state estimate, Eq. 15.4, is based on a linear combination of the weighted measurement residual and the last state estimate.

$$\hat{x}_{\bar{k}} = x_{k-1} + 0.5(x_{k-1} - x_{k-3}) + 0.5(x_{k-1} - 2x_{k-2} + x_{k-3}) \quad (15.1)$$

$$P_{\bar{k}} = P_{k-1} + Q_k \quad (15.2)$$

$$K_k = \frac{P_{\bar{k}}}{(P_{\bar{k}} + R_k)} \quad (15.3)$$

The new error covariance projector, Eq. 15.2, is it's previously computed value combined with the current process noise covariance, $Q_k$, which is tuned by an example model derived from the measured motion dynamics shown in Eq. 16.1. The gain's measurement noise covariance, $R_k$, is defined as a small constant and based upon the actual static timing variance empirically measured. The smaller this value the more confidence there exists in the systems' measurement capability.

In the preferred embodiment, the product of the numerically-derived $1^{st}$ and $2^{nd}$ order derivatives of the measured position scaled by a frequency dependent gain provides a computationally practical adaptive dynamic process noise estimate model. The derivative product term increases $Q_k$ proportionally for higher velocity and acceleration components of motion, e.g., quick, abrupt directional changes, which effectively increases the gain and, therefore, means more confidence exists in the measurement rather than the estimate. This provides faithful, low-latency response to high-frequency motions. Conversely, the frequency scaling term decreases the predictive "overshoot" characteristic of lower power, repetitive motion, e.g. slower, cyclic, ROM trajectories, which effectively decreases the gain and, therefore, means more confidence exists in the estimate rather than the measurement. It should be appreciated this filter implementation provides superior tracking fidelity and comparable smoothing characteristics as compared to practical lengths of finite impulse response running-average filters and various low-orders infinite impulse response filters. It achieves enough predictive response to compensate for the inherent TOF and computation latencies, while providing comparable smoothing properties of other filter types.

$$Q_k = |K_q[(z_{k-1} - z_{k-3})(z_{k-1} - 2z_{k-2} + z_{i-3})\sin(z_{k-1} - z_{k-3})]| \quad (16.1)$$

$$R_k = 0.005 \quad (16.2)$$

In the preferred embodiment, a three dimensional (3D) piecewise cubic curve interpolates a movement trajectory for smoothing and reduced sample storage for greater memory efficiency. Preferably, four (4) sequential discrete control points of the n-length set of control points, the sample resolution dependent upon the desired movement granularity, and corresponding timestamp are needed to calculate in real-time the interpolated position between any pair of control points. A Catmull-Rom spline algorithm is the preferred method in that the path intersects the control points and would best approximate a movement that may have acute directional changes. The Catmull-Rom spline algorithm is defined by Eqs. 17.1-3, where the geometry matrix $G_k$ represents the matrix of three dimensional (3D) control points.

$$C_k(\mu) = G_k \frac{1}{2}\begin{bmatrix} 0 & -1 & 2 & -1 \\ 2 & 0 & -5 & 3 \\ 0 & 1 & 4 & -3 \\ 0 & 0 & -1 & 1 \end{bmatrix}\begin{bmatrix} 1 \\ \mu \\ \mu^2 \\ \mu^3 \end{bmatrix} \quad (17.1)$$

$$C_k(\mu) = G_k \begin{bmatrix} -0.5\mu + \mu^2 - 0.5\mu^3 \\ 1 - 2.5\mu^2 + 1.5\mu^3 \\ 0.5\mu + 2\mu^2 - 1.5\mu^3 \\ -0.5\mu^2 + 0.5\mu^3 \end{bmatrix} \quad (17.2)$$

$$G_k \equiv [P_{k-1} \; P_k \; P_{k+1} \; P_{k+2}] \quad (17.3)$$

The $\mu$ value is normalized and represents the % value between the $2^{nd}$ $3^{rd}$ control points. To calculate the interpolated value between the $1^{st}$ and $2^{nd}$ or the n-$1^{th}$ and n$^{th}$ control points, the value of first control point of the pair and the value of the last control point pair are doubly entered into the geometry matrix, respectively. The appropriate dp/dt is determined by the desired rate of playback of movement trajectory. To playback at the same rate as the recorded session, and assuming fairly constant velocity, a timestamp should also be saved at each control point registration so that the $\mu$ calculation is correctly scaled by the delta time interval. The n-length set of control points would be manually registered by the user pressing a switch or automatically post processed by a sorting method where a control point is registered at the tangents of the trajectory having sufficient magnitude and/or experience sign changes which indicates discontinuous or non-monotonic movement.

The major functional interfaces of the transponder unit preferably include the sensory interface, transducer interface, processor, and communication interface. The following descriptions of the transponder unit are based upon the dependence flow represented by FIG. 6.

The sensor interface refers to the collective support for the ultrasonic transmitter, heart rate receiver, and accelerometer circuits. The ultrasonic transmitter circuit is preferably gated by a pulse-width modulated (PWM) digital signal at nominally 0.8% duty cycle of the 40 kHz resonant frequency, e.g., a single 250 µs pulse every analysis period, by the processor circuit. The radiated ultrasonic signal strength is controlled by gating a MOSFET transistor switch at a duty cycle which optimally energizes the transducer's series resonant tank circuit for sufficient duration. The resonant circuit's reactive components include an impedance matching inductor, the transducer's intrinsic capacitance, and a small damping resistive load. At resonance, a electrical damped sinusoidal with a potential up to ~400 $V_{pk-pk}$ is developed across the transducer to sufficiently drive it at acoustical power levels practical for the system's intended range of operation. Enabling a lower duty cycle control through means of a software algorithm monitoring the transponders range would effectively lower the transponders power consumption and radiate less ultrasonic acoustic energy for close range operation when signal saturation and clipping is undesirable. Conversely, a higher duty cycle control would radiate greater ultrasonic energy to compensate for less efficient, non-optimal acoustical coupling orientations of the transponder with respect to the receiver constellation. Optionally, two additional transducers may be driven in unison or sequentially from a different transponder assembly to support measurement of absolute rotation about a single or multiple axes, or provide calculated positional redundancy for certain difficult line-of-sight applications.

The heart rate receiver circuit wirelessly receives a 5 kHz heart rate signal from a POLAR® transmitter belt. The transmitter, worn around the chest, electrically detects the heart beat and starts transmitting a pulse corresponding to each heart beat. The receiver captures the signal and generates a corresponding digital pulse which is received by the timing capture-control circuit of the processor interface. A software algorithm processes the signal with known time-based averaging and an adaptive window filter techniques to remove any extraneous artifact or corruption caused by interfering sources.

The accelerometer circuit consists of a low cost +/−1.5 g dual axis accelerometer that can measure both dynamic, e.g. vibration, and static, e.g. gravity or tilt, acceleration. If the accelerometer is oriented so both its axes are parallel to the earth's surface it can be used as a two axis tilt sensor with a roll and pitch axis.

The stimuli interface circuit provides the primary visual sensory interface preferably comprised of a linear array of five (5) bright, white light emitting diodes (LED) and associated drivers. The preferred LED device is a CMD87 manufactured by Chicago Miniature Lamp. These LEDs' intensity is controlled by a white LED driver. The preferred white LED driver device is a MAX 1570 manufactured by Maxim. The white LED driver provides a maximum 120 mA constant current source to each LED for optimal uniform luminescence. The drive current can be proportionally regulated through external pulse width modulation (PWM) means from the processor circuit to modulate its brightness level. Additionally, an electronic switch is connected in series to each LED drive to individually control its active state. By simultaneously controlling the PWM duty cycle and active state of each LED, the light strobe can appear to smoothly migrate along the linear array in spite of its discontinuous operation.

Preferably, the stimuli interface circuit provides the primary aural stimulus by means of a 4 kHz piezo buzzer. The preferred device is SMT-3303-G manufactured by Projects Unlimited. This electro-mechanical buzzer requires an external transistor drive circuit and digital control signal gated at a rate near its resonant frequency. The buzzer inputs are connected to and controlled by PWM means from the processor circuit to provide a gross volume adjustment which is dependent upon the amplitude of the drive signal.

Additionally, the stimuli interface circuit provides the primary tactile stimulus by means of a vibrator motor. The driver for the vibrator motor enables a 120 mA DC current source to excite the motor armature. The preferred driver device is the MAX 1748 manufactured by Maxim. The rotational speed of the motor's armature is controlled by PWM means from the processor circuit.

The processor circuit preferably receives input from the stimuli interface, sensor interface, and the communication interface and provides controlling signals therein. The preferred processor circuit is the MC9S08 GB60 which is manufactured by Motorola Inc. It is a low-cost, high-performance 8-bit microcontroller device that integrates the specialized hardware circuits into one convenient device. The software calculation engine circuit operates from an embedded 60 KB FLASH for program memory with in-circuit programmable capability and 4 KB RAM for data memory. The time base circuit is preferably comprised of an external, high-noise immunity, 4.0 MHz system clock, which multiplies this value by the internal frequency-locked loop for a bus clock of 40.0 MHz and single instruction execution time of 25 ηS. This clock also provides all the capture and control timing requirements for the other specified circuits. Multiple parallel I/O ports and dedicated asynchronous serial communication signals provide digital control for the circuits of the parallel/serial I/O circuit.

In the preferred embodiment, the graphic LCD and touch screen circuit is the primary user input device for database management for an interactive transponder configuration. For example, it may be a 128×64 graphical liquid crystal display system (LCD) and associated 4-pin touch screen input device. A preferred LCD device is the 51553 manufactured by Optrex and the preferred touch screen device is the TSG-51 manufactured by Apollo Displays. LCD display information, configuration commands, and bitmaps images can be loaded through the software calculation engine via a parallel memory interface to emulate a graphical user interface. A touch screen input device is connected to a controller circuit to decode soft key presses at areas over the graphical object. Preferably, the key presses are registered, filtered, decoded, and processed by the controller and then transferred to the software calculation engine via an interrupt driven asynchronous serial communication channel of the I/O interface. A preferred LCD controller is the UR7HCTS manufactured by Semtech.

The timing capture-control circuit provides controlling means for the stimuli interface and portions of the sensor interface. The stimuli interface is preferably comprised of a five channel 16-bit timer PWM module with programmable interrupt control which provides 250 ηs timing resolution to automatically modulate the circuits' drivers through variable duty cycle control.

In the preferred embodiment, the A/D conversion circuit receives the output from the accelerometer circuit and consists of a two channel 10-bit analog-to-digital converter used to determine the rotational angle of roll and pitch in the accelerometer deviates from its horizontal plane orientation. This information is communicated to the signal processor via the radio link.

In the preferred embodiment, the radio link circuit is comprised of a wireless bi-directional communication interface (with a receiver and transmitter shown generally at 20 and 30) to (1) receive a synchronization signal for control of the transponders interoperability, (2) to transfer acquired local sensor data, including, but not limited to, accelerometer, heart rate, battery, user I/O status, to processor unit and (3) to provide means to configure its local database from command of processor unit. The preferred wireless communication link is based upon the AT86RF211, a highly integrated, low-power FSK transceiver optimized for license-free ISM band operations from 400 MHz to 950 MHz and manufactured by Atmel. Its key features are described above.

In the preferred embodiment, the switch I/O circuit uses a SPST push button switch for user input to control the system's operational states, start and stop program execution, and function as feedback input to the program. A preferred device is the KSS231 SPST push button switch manufactured by ITT Industries.

What is claimed is:

1. A system for a user to play a video game, comprising:
a first hand-held communication device comprising:
a transmitter for transmitting signals;
a receiver for receiving signals;
an output device;
a motion detector; and
a user input device resident on the first hand-held communication device; and
a processing system, remote from the first hand-held communication device, adapted to wirelessly receive the signals transmitted by the transmitter, to determine motion information for the first hand-held communication device, and to send data signals to the first hand-held device to provide feedback data to the user, wherein the output device responds to the feedback data;

wherein the motion information of the first hand-held communication device affects movement of at least one object in a computer generated virtual environment; and
wherein the first hand-held communication device is adapted to receive and process the data signals and generate sensory stimuli for the user based on the data signals and delivered through the output device.

2. The video game system of claim 1, further comprising:
a second hand-held communication device adapted to electrically communicate with the first hand-held communication device, said second hand-held communication device, comprising a transmitter for transmitting signals;
wherein the processing system is adapted to determine motion information of the second hand-held communication device.

3. The video game system of claim 2, wherein the feedback data sent to the receiver is derived from the motion information of the first hand-held communication device and the second hand-held communication device.

4. The video game system of claim 3, wherein the output device provides audible stimuli to the user based on the feedback data.

5. The video game system of claim 2, wherein the processing system determines motion information for the first hand-held communication device and the second hand-held device and processes this information to provide feedback data to the user.

6. The video game system of claim 5, wherein the motion information for the first and second hand-held devices is processed to provide feedback data to the user based on the motion of the first hand-held communication device with respect to the second hand-held communication device.

7. The video game system of claim 2, wherein the processing system is adapted to determine position information for the first hand-held communication device and process this position information to provide feedback data to the user.

8. The video game system of claim 2, wherein the first hand-held communication device is adapted to attach to a modular extension piece.

9. The video game system of claim 1, wherein the first hand-held communication device is further comprised of:
a tilt sensor for sensing orientation data for the first hand-held communication device, and wherein the first hand-held communication device transmits the orientation data to the processing system.

10. The video game system of claim 9, wherein the orientation data is roll and pitch data and wherein the feedback data sent to the receiver is derived from the orientation data.

11. The video game system of claim 1, wherein the user input device is a touch screen display for accepting input from the user.

12. The video game system of claim 11, wherein the first hand-held communication device is adapted to allow the user to provide configuration data to the system through the touch screen display.

13. The video game system of claim 1, wherein the user input device is a touch screen display for accepting input from the user for interaction between the first communication device and the remote processing system.

14. The video game system of claim 1, wherein the system is interactive and responds to verbal command input from the user.

15. The video game system of claim 1, wherein the first hand-held communication device is adapted to attach to a modular extension piece.

16. The video game system of claim 15, wherein the modular extension piece is a sensory instrument.

17. The video game system of claim 1, wherein the user input device is adapted to calibrate the system.

18. The video game system of claim 1, wherein the system is adapted to activate the output device based on the movement information for the first hand-held communication device.

19. The video game system of claim 1, wherein the system is adapted to activate the output device to indicate the quality of movement information for the first hand-held communication device.

20. The video game system of claim 1, wherein the system is adapted to proportionally activate the output device based on the movement information for the first hand-held communication device.

21. The video game system of claim 1, wherein the system is adapted to provide feedback data to the output device when the user has completed an activity.

22. The video game system of claim 1, wherein the system is adapted to modulate activity challenges based on scoring criteria.

23. The video game system of claim 1, wherein the system is adapted to visually cue the user to move according to a desired movement trajectory to assess balance control.

24. The video game system of claim 1, wherein the system is interactive and provides real-time projection of verbal command output to the user.

25. The video game system of claim 1, wherein the system is adapted to cue the user to control range of motion within prescribed limits.

26. The video game system of claim 1, wherein the system is adapted to provide feedback data to the output device when the user deviates from a desired movement trajectory.

27. The video game system of claim 1, wherein the system is interactive and responds to verbal command input from the user to modulate an activity.

28. The video game system of claim 1, further comprising:
a second hand-held communication device in electrical communication with the first hand-held communication device, said second hand-held communication device, comprising a transmitter for transmitting signals,
wherein the processing system is adapted to determine motion information of the second hand-held communication device; and
wherein the motion information of the first hand-held communication device and the second hand-held communication device is used to derive performance measurements of functional movements.

29. The video game system of claim 28, wherein functional movements can be measured of gait, jumping, cutting, turning, or shuttling.

30. The video game system of claim 28, wherein the functional movement measured can be balance or stance.

31. The video game system of claim 1, wherein the processing system is adapted to determine the position of the first hand-held communication device and wherein the first hand-held communication device controls a graphical object in a virtual three-dimensional environment.

32. A system for a user to play a video game, comprising:
a first hand-held communication device comprising:
a transmitter for transmitting signals;
a receiver for receiving signals;
an output device; and
a user input device;
a processing system, remote from the first hand-held communication device for wirelessly receiving the signals transmitted by the transmitter, determining orientation information for first hand-held communication device; and a second hand-held communication device, in wireless communication with the processing system said second hand-held communication device, comprising a transmitter for transmitting signals;

wherein the processing system is adapted to process orientation information of the second hand-held communication device and send feedback data to the user based on the orientation information of the first and second hand-held communication devices;

wherein the first hand-held communication device is adapted to receive and process the feedback data and generate sensory stimuli for the user based on the received data and delivered through the output device; and wherein the orientation information of the first and second hand-held communication devices is used to control a graphical object on a display screen.

33. The video game system of claim 32, wherein the system is interactive and responds to verbal command input from the user to modulate an activity.

34. The video game system of claim 32, wherein the system is adapted to visually cue the user to move according to a desired movement trajectory to assess balance control.

35. The video game system of claim 32, wherein the system is interactive and provides real-time projection of verbal command output to the user.

36. The video game system of claim 32, wherein the user input device is touch screen display for accepting input from the user.

37. The video game system of claim 36, wherein the user input device is adapted to allow the user to provide configuration data to the system through the touch screen display.

38. The video game system of claim 36, wherein the system is adapted to provide feedback data to the user through the touch screen display.

39. The video game system of claim 36, wherein the system is adapted to provide performance data to the user through the touch screen display.

40. The video game system of claim 36, wherein the system is adapted to allow system setup through the touch screen display.

41. The video game system of claim 36, wherein the system is adapted to provide a menu oriented interface to the user through the touch screen display.

42. The video game system of claim 36, wherein the system is adapted to allow program selection to the user through the touch screen display.

43. The video game system of claim 36, wherein the system is adapted to display biophysical data to the user through the touch screen display.

44. A system according to claim 32, wherein:
the first hand-held communication device is adapted to attach to a modular extension piece.

45. A system according to claim 44, wherein the second hand-held communication device is adapted to attach to the modular extension piece.

46. A system according to claim 44, wherein the first hand-held communication device is connected to the modular extension piece via a flexible coupling.

47. A system according to claim 44, wherein the modular extension piece is a sensory instrument.

48. A system according to claim 32, wherein the user input device is adapted to calibrate the system.

49. A system for a user to play a video game, comprising:
a first hand-held communication device comprising:
a transmitter for transmitting signals;
a receiver for receiving signals;
an output device; and
a user input device; and
a processing system, remote from the first hand-held communication device, adapted to wirelessly receive the signals transmitted by the transmitter, to process movement information in one dimension for the first hand-held communication device and to transmit control or feedback data signals to the first hand-held communication device;

wherein the movement information in one dimension of the first hand-held communication device affects the movement of at least one object in a computer generated virtual environment;

wherein the first hand-held communication device is adapted to receive and process the data signals and generate sensory stimuli for the user based on the data signals and delivered through the output device.

50. A system for a user to play a video game, comprising:
a first hand-held communication device comprising:
a transmitter for transmitting signals;
a receiver for receiving signals;
a user input device; and
an output device;
a second hand-held communication device, the second hand-held communication device comprising a transmitter for transmitting signals; and
a processing system, remote from the first hand-held communication device, adapted to wirelessly receive the signals transmitted by the transmitters of the respective communication devices, to process motion information for each of the respective communication devices, and to send data signals to the receiver to provide feedback data to the user, wherein the output device responds to the feedback data;

wherein the first hand-held communication device is adapted to receive and process the data signals and generate sensory stimuli for the user based on the data signals and delivered through the output device;

wherein the motion information of the first and second hand-held devices are used to control a graphical object on a display screen; and wherein the system is interactive and responds to verbal command input from the user.

51. A system according to claim 50, wherein the first hand-held communication device is adapted to attach to a modular extension piece.

52. The system of claim 51, wherein the modular extension piece is a sensory instrument.

53. The system of claim 51, wherein the modular extension piece is a weighted extension.

54. The system of claim 50, wherein the user input device is adapted to calibrate the system.

55. A system according to claim 50, further comprising:
a strap connected to the first hand-held communication device for securing the first hand-held communication device to a user's limb.

56. A system according to claim 50, wherein:
The first hand-held communication device comprises a user input device adapted for communication with the processing system through the transmitter.

57. A system according to claim 56, wherein:
the user input device is adapted for calibrating the first communication device to establish a reference position.

58. A system according to claim 50, wherein:
the processing system is adapted to determine movement information for each of the respective communication devices.

59. The video game system of claim 50, wherein user input device is a touch screen display for accepting input from the user.

60. The video game system of claim 59, wherein the touch screen display allows for interaction between the first communication device and the remote processing system.

61. A system according to claim 50, further comprising:
a coupling attachment to the first hand-held communication device adapted to accept attachment to the second hand-held communication device.

62. A system according to claim 50, further comprising:
a coupling attachment to the first hand-held communication device adapted to accept attachment to a modular extension piece.

63. A system for a user to play a video game, comprising:
a first hand-held communication device comprising:
a transmitter for transmitting signals;
a receiver for receiving signals;
an accelerometer;
an output device, and
a user input device;
a second hand-held communication device adapted to electrically communicate with the first communication device, and adapted for being attached to, in contact with, or held by the user; and
a processing system, remote from the first hand-held communication device, adapted to wirelessly receive the signals transmitted by the transmitter of the first hand-held communication device, to process acceleration information for each of the respective communication devices, and to send data signals to the receiver to provide feedback data to the user, wherein the output device responds to the feedback data;
wherein the first hand-held communication device is adapted to receive and process the data signals and generate sensory stimuli for the user based on the data signals, the sensory stimuli delivered through the output device.

64. A system according to claim 63, wherein:
the processing system is adapted to determine movement information for each of the respective communication devices.

65. The video game system of claim 63, wherein the system is interactive and provides real-time projection of verbal command output to the user.

66. A system according to claim 63, wherein:
the first hand-held communication device is adapted to attach to a modular extension piece.

67. A system according to claim 66, wherein the second hand-held communication device is adapted to attach to the modular extension piece.

68. A system according to claim 66, wherein the modular extension piece is a sensory instrument.

69. A system according to claim 63, wherein the user input device is adapted to calibrate the system.

70. The video game system of claim 63, wherein the user input device is a touch screen display for accepting input from the user.

71. The video game system of claim 70, wherein the touch screen display allows for interaction between the first communication device and the remote processing system.

72. A system for a user to play a video game, comprising:
a first hand-held communication device comprising:
a transmitter for transmitting signals;
a receiver for receiving signals;
a user input device and an output device;
a second hand-held communication device adapted to electrically communicate with the first communication device, and adapted for being attached to, in contact with, or held by the user, the second hand-held communication device comprising a transmitter for transmitting signals; and
a processing system, remote from the first hand-held communication device, adapted to wirelessly receive the signals transmitted by the transmitter of the first hand-held communication device, and to send data signals to the receiver to provide feedback data to the user, wherein the output device responds to the feedback data;
wherein the first hand-held communication device receives and processes the data signals and generates sensory stimuli for the user based on the data signals and delivered through the output device;
wherein the user input device adapted for communication with the processing system through the transmitter; and
wherein the user input device is adapted to provide configuration data to the system.

73. A system according to claim 72, wherein:
the processing system is adapted to determine movement information for each of the respective communication devices.

74. The video game system of claim 72, wherein the user input device is a touch screen display for accepting input from the user.

75. The video game system of claim 74, wherein the system is adapted to provide feedback data to the user through the touch screen display.

76. The video game system of claim 74, wherein the system is adapted to provide performance data to the user through the touch screen display.

77. The video game system of claim 74, wherein the system is adapted to allow system setup through the touch screen display.

78. The video game system of claim 74, wherein the system is adapted to provide a menu oriented interface to the user through the touch screen display.

79. The video game system of claim 74, wherein the system is adapted to allow program selection to the user through the touch screen display.

80. The video game system of claim 74, wherein the system is adapted to display biophysical data to the user through the touch screen display.

81. A system according to claim 74, wherein the touch screen display allows for interaction between the first communication device and the remote processing system.

82. The video game system of claim 72, wherein the user input device is adapted to allow the user to provide calibration data to the system.

83. A system according to claim 72, wherein:
the first hand-held communication device is adapted to attach to a modular extension piece.

84. A system according to claim 83, wherein the first hand-held communication device is connected to the modular extension piece via a flexible coupling.

85. A system for a user to play a video game, comprising:
a first hand-held communication device comprising:
a transmitter for transmitting signals;
a receiver for receiving signals;
an output device; and a user input device; and a processing system, remote from the first hand-held communication device, adapted to wirelessly receive the signals transmitted by the transmitter, to process motion information in one dimension for the first hand-held communication device and to transmit control or feedback data signals to the first hand-held communication device;

wherein the motion information in one dimension of the first hand-held communication device affects the motion of at least one object in a computer generated virtual environment;

wherein the first hand-held communication device is adapted to receive and process the data signals and generate sensory stimuli for the user based on the data signals and delivered through the output device.

86. The video game system of claim 85, wherein the system is interactive and provides real-time projection of verbal command output to the user.

87. The video game system of claim 85, wherein the processing system further processes orientation information in one dimension for the first-hand held communication device and wherein the processing system is adapted to transmit data signals to the first hand-held communication device based on the orientation information.

88. The video game system of claim 85, wherein the processing system further processes position information in one dimension for the first-hand held communication device and wherein the processing system is adapted to transmit data signals to the first hand-held communication device based on the position information.

89. A system for a user to play a video game, comprising:
a first hand-held communication device comprising:
a transmitter for transmitting signals;
a receiver for receiving signals;
an output device; and
a user input device; and
a processing system, remote from the first hand-held communication device, adapted to wirelessly receive the signals transmitted by the transmitter, to process position information in one dimension for the first hand-held communication device and to transmit control or feedback data signals to the first hand-held communication device;

wherein the position information in one dimension of the first hand-held communication device affects the position of at least one object in a computer generated virtual environment;

wherein the first hand-held communication device is adapted to receive and process the data signals and generate sensory stimuli for the user based on the data signals and delivered through the output device.

90. The video game system of claim 89, wherein the system is interactive and provides real-time projection of verbal command output to the user.

91. The video game system of claim 89, wherein the user input device is adapted to calibrate the system.

92. The video game system of claim 89, wherein the processing system further processes orientation information in one dimension for the first-hand held communication device and wherein the processing system is adapted to transmit data signals to the first hand-held communication device based on the orientation information.

93. The video game system of claim 89, wherein the processing system further processes motion information in one dimension for the first-hand held communication device and wherein the processing system is adapted to transmit data signals to the first hand-held communication device based on the motion information.

94. A system for a user to play a video game, comprising:
a first hand-held communication device comprising:
a transmitter for transmitting signals;
a receiver for receiving signals;
an output device;
a motion detector; and
a user input device resident on the first hand-held communication device; and
a processing system, remote from the first hand-held communication device, adapted to wirelessly receive the signals transmitted by the transmitter and adapted to determine motion information for the first hand-held communication device, and
wherein the first hand-held communication device is adapted to generate sensory stimuli delivered through the output device.

95. The video game system of claim 94, further comprising:
a second hand-held communication device adapted to electrically communicate with the first hand-held communication device, said second hand-held communication device, comprising a transmitter for transmitting signals.

96. The video game system of claim 95, wherein the sensory stimuli is derived from the motion information of the first hand-held communication device.

97. The video game system of claim 94, wherein the first hand-held communication device is further comprised of:
a tilt sensor for sensing orientation data for the first hand-held communication device.

98. The video game system of claim 97, wherein the orientation data is roll and pitch data and wherein the sensory stimuli is derived from the orientation data.

99. The video game system of claim 94, wherein the output device provides audible stimuli to the user.

100. The video game system of claim 94, wherein the user input device is a touch screen display for accepting input from the user.

101. The video game system of claim 100, wherein the first hand-held communication device is adapted to allow the user to provide configuration data to the system through the touch screen display.

102. The video game system of claim 94, wherein the user input device is a touch screen display for accepting input from the user for interaction between the first communication device and the remote processing system.

103. The video game system of claim 94, wherein the system is interactive and responds to verbal command input from the user.

104. The video game system of claim 94, wherein the first hand-held communication device is adapted to attach to a modular extension piece.

105. The video game system of claim 94, wherein the user input device is adapted to calibrate the system.

106. The video game system of claim 104, wherein the modular extension piece is a sensory instrument.

107. The video game system of claim 94, wherein the system is interactive and provides real-time projection of verbal command output to the user.

* * * * *